United States Patent
Wade

(10) Patent No.: US 10,695,308 B2
(45) Date of Patent: *Jun. 30, 2020

(54) INHALATION FORMULATIONS OF TREPROSTINIL

(71) Applicant: United Therapeutics Corporation, Silver Spring, MD (US)

(72) Inventor: Michael Wade, Chapel Hill, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/131,248

(22) Filed: Sep. 14, 2018

(65) Prior Publication Data

US 2019/0231722 A1    Aug. 1, 2019

Related U.S. Application Data

(63) Continuation of application No. 15/657,933, filed on Jul. 24, 2017, now Pat. No. 10,076,505, which is a continuation of application No. 14/629,938, filed on Feb. 24, 2015, now Pat. No. 9,713,599, which is a continuation of application No. 12/232,611, filed on Sep. 19, 2008, now abandoned, which is a continuation-in-part of application No. 11/012,723, filed on Dec. 16, 2004, now Pat. No. 8,765,813.

(60) Provisional application No. 60/529,622, filed on Dec. 16, 2003.

(51) Int. Cl.
| | |
|---|---|
| A61K 31/192 | (2006.01) |
| A61K 31/191 | (2006.01) |
| A61K 31/201 | (2006.01) |
| A61K 31/557 | (2006.01) |
| A61K 31/57 | (2006.01) |
| A61K 31/19 | (2006.01) |

(52) U.S. Cl.
CPC .......... *A61K 31/192* (2013.01); *A61K 31/191* (2013.01); *A61K 31/201* (2013.01); *A61K 31/557* (2013.01); *A61K 31/19* (2013.01); *A61K 31/57* (2013.01)

(58) Field of Classification Search
CPC ............................... A61K 31/19; A61K 31/57
USPC ........................................................ 514/171
See application file for complete search history.

(56) References Cited

U.S. PATENT DOCUMENTS

| | | | |
|---|---|---|---|
| 4,254,145 A | 3/1981 | Birnbaum | |
| 4,281,113 A | 7/1981 | Axen et al. | |
| 4,306,075 A | 12/1981 | Aristoff | |
| 4,306,076 A | 12/1981 | Nelson | |
| 4,338,457 A | 7/1982 | Aristoff | |
| 4,349,689 A | 9/1982 | Aristoff | |
| 4,486,598 A | 12/1984 | Aristoff | |
| 4,668,814 A | 5/1987 | Aristoff | |
| 4,683,330 A | 7/1987 | Aristoff | |
| 4,692,464 A | 9/1987 | Skuballa et al. | |
| 4,708,963 A | 11/1987 | Skuballa et al. | |
| 4,895,719 A | 1/1990 | Radhakrishnan et al. | |
| 5,153,222 A | 10/1992 | Tadepalli et al. | |
| 5,190,972 A | 3/1993 | Dumble | |
| 5,234,953 A | 8/1993 | Crow et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,756,033 B2 | 6/2004 | Cloutier et al. | |
| 7,417,070 B2 | 8/2008 | Phares et al. | |
| 7,544,713 B2 | 6/2009 | Phares et al. | |
| 9,713,599 B2 * | 7/2017 | Wade .................. | A61K 31/191 |
| 2002/0019350 A1 | 2/2002 | Levine et al. | |
| 2004/0105819 A1 | 6/2004 | Hale et al. | |
| 2004/0265238 A1 | 12/2004 | Chaudry | |

FOREIGN PATENT DOCUMENTS

| | | |
|---|---|---|
| AU | 1999959533 B2 | 2/2000 |
| CA | 1 201 712 A | 3/1986 |
| EP | 0 159 784 A1 | 10/1985 |
| EP | 0 159 784 B1 | 6/1989 |
| EP | 0 347 243 A1 | 12/1989 |
| EP | 1 161 234 B1 | 12/2001 |
| GB | 2 070 596 A | 9/1981 |
| JP | 56-138130 A | 10/1981 |
| JP | 60-208936 A | 10/1985 |

(Continued)

OTHER PUBLICATIONS

Simonneau et al., Continuous Subcutaneous Infusion of Treprostinil, a Prostacyclin Analogue, in Patients with Pulmonary Arterial Hypertension:, American Journal of Respiratory and Critical Care Medicine, vol. 165, No. 6, pp. 800-804 (2002).*

Gibbs, "Chronic Infusion of Treprostinil is Safe and Appears to Prolong Survival over a Three-Year Period in Patient with Pulmonary Arterial Hypertension", Circulation, vol. 106, No. 19, Supplemental, pp. II-575 (2002).*

Abe et al., "Effects of inhaled prostacyclin analogue on chronic hypoxic pulmonary hypertension," J. Cardiovascular Pharmacology, 2001, 37, 239 251.

Aristoff et al., "Synthesis of benzopyran prostaglandins, potent stable prostacyclin analogs, via an intermolecular mitsunobu reaction," Tetrahedron Letters, 1984, 25(36):3955-3958.

(Continued)

*Primary Examiner* — Kevin E Weddington
(74) *Attorney, Agent, or Firm* — Foley & Lardner LLP

(57) ABSTRACT

The present invention describes novel methods for using Treprostinil or its derivative, or a pharmaceutically acceptable salt thereof, for the treatment and/or prevention of ischemic lesions, such as digital ulcers, in subjects with scleroderma (including systemic sclerosis), Buerger's disease, Raynaud's disease, Raynaud's phenomenon and/or other conditions that cause such lesions. The invention also relates to kits for treatment and/or prevention of ischemic lesions, comprising an effective amount of Treprostinil or its derivative, or a pharmaceutically acceptable salt thereof.

3 Claims, 26 Drawing Sheets

(56) References Cited

FOREIGN PATENT DOCUMENTS

| JP | 02-040325 A | 2/1990 |
|---|---|---|
| JP | 2003-523935 A | 8/2003 |
| WO | WO 99/25357 A | 5/1999 |
| WO | WO 00/54758 A2 | 9/2000 |
| WO | WO 00/57701 A1 | 10/2000 |
| WO | WO 2004/019952 A | 3/2004 |
| WO | WO 2005/007081 A | 1/2005 |

OTHER PUBLICATIONS

Bein et al., "Cardiovascular and pulmonary effects of aerosolized prostacyclin administration in severe respiratory failure using a ventilator nebulization system," J. Cardiovascular Pharmacology, 1996, 27, 583-586.
Benedict et al., "Evidence-based pharmacologic management of pulmonary arterial hypertension," Clinical Therapeutics, 2007, 29, 2134-2153.
Benthin, N. P., "Ilomedin (iloprost) og mb. Buerger", Ugeskr Laeger, vol. 157, No. 36, pp. 4946-4947 (1995).
Bindl et al., "Aerosolised prostacyclin for pulmonary hypertension in neonates," Archives of disease in childhood, Fetal and neonatal edition, 1994, 71(3), F214-6.
Brock et al., "Iloprost in der Behandlung ischämischer Gewebsläsionen bei Diabetikern," Schweiz. Med. Wschr., 1990, 120(40):1477-1482, with English summary.
Brooke et al., Anesth. Analg., 1998, 86:917.
Channick et al., "Safety and efficacy of inhaled treprostinil as add-on therapy to bosentan in pulmonary arterial hypertension," J. American College of Cardiology, 2006, 48, 1433-1437.
Chattaraj, Sarat C., "Treprostinil sodium Pharmacia," Current Opinion in Investigational Drugs, Apr. 2002, 3(4):582-586.
Clapp, L. H., et al., "Differential Effects of Stable Prostacyclin Analogs on Smooth Muscle Proliferation and Cyclic AMP Generation in Human Pulmonary Artery", Am. J. Respir. Cell Mol. Biol., vol. 26, pp. 194-201 (2002).
Creutzig et al., "Prostanoids in therapy of peripheral arterial occlusive disease," Therapie, 1991, 46:241-245, with English summary.
Doyle et al., "Inhaled prostacyclin as a selective pulmonary vasodilator," Anaesthesia and Intensive Care, Aug. 1996, 24(4):514-515.
Dumas et al,. "Hypoxic pulmonary vasoconstriction," General Pharmacology, 1999, 33, 289-297.
Dworetz et al., "Survival of infants with persistent pulmonary hypertension without extracorporeal membrane oxygenation," Pediatrics, 1989, 84, 1-6.
Dworetz et al., "Survival of Infants With persistent Pulmonary Hypertension Without Extracorporeal Membrane Oxygenation," Pediatrics, 1989, 84(1):1-6.
Engel et al., "Treprostinil for the treatment of severe digital necrosis in systemic sclerosis," Vascular Medicine, 2005, 10:29-32.
Ewert et al., "Aerosolized iloprost for primary pulmonary hypertension," New England Journal of Medicine, 2000, 343, 1421-1422.
Ewert et al., "Iloprost als inhalative bzw. Intravenose langzeitbehandlung von patienten mit primarer pulmonaler hypertonie," Z. Kardiol., 2000, 89, 987-999.
Fiessinger, J. N., et al., "Trial of iloprost versus aspirin treatment for critical limb ischaemia of thromboangiitis obliterans", the Lancet, vol. 335, no. 8689, pp. 555-557 (1990).
Fink et al., "Use of Prostacyclin and its Analogues in the Treatment of Cardiovascular Disease," Heart Disease, 1999, 1:29-40.
Fox et al., "Pulmonary Hypertension in the Perinatal Aspiration Syndromes," Pediatrics, 1977, 59(2):205-211.
Gessler et al., "Ultrasonic versus jet nebulization of iloprost in severe pulmonary hypertension," Eur. Respir. J., 2001, 17, 14-19.
Haraldsson et al., "Comparison of inhaled nitric oxide and inhaled aerosolized prostacyclin in the evaluation of heart transplant candidates with elevated pulmonary vascular resistance," Chest, 1998, 114, 780-786.

Hoeper et al., "A comparison of the acute hemodynamic effects of inhaled nitric oxide and aerosolized iloprost in primary hypertension," J. American College of Cardiology, 2000, 35, 176-182.
Hoeper et al., "Effects of inhaled nitric oxide and aerosolized iloprost in pulmonary veno-occlusive disease," Respiratory Medicine, 1999, 93, 62-70.
Hoeper et al., "Long term treatment of primary pulmonary hypertension with aerosolized iloprost, a prostacyclin analogue," New England Journal of Medicine, 2000, 342, 1866-1870.
Howarth, P.N., "Why particle size should affect clinical response to inhaled therapy," Journal of Aerosol Medicine, 2001, 14 Supp. 1, S-27-S-34.
Hummers et al,. "Management of Raynaud's phenomenon and digital ischemic lesions in scleroderma," Rheum. Dis. Clin. North Amer., May 2003, 29(2):293-313, full article.
Ichida et al., "Additive effects of beraprost on pulmonary vasodilation by inhaled nitric oxide in children with pulmonary hypertension," American Journal of Cardiology, 1997, 80, 662-664.
Krause et al., "Pharmacokinetics and pharmacodynamics of the prostacyclin analogue iloprost in man," Eur. J. Clin. Pharmacol., 1986, 30, 61-68.
Kyle, M. V., et al., "Placebo Controlled Study Showing Therapeutic Benefit of Iloprost in the Treatment of Raynaud's Phenomenon", The Journ. of Rheumatol., vol. 19, No. 9, pp. 1403-1406 (1992).
Langevitz et al., "Treatment of Refractory Ischemic Skin Ulcers in Patients with Raynaud's Phenomenon with $PGE_1$ Infusions," The Journal of Rheumatology, 1989, 16(11):1433-1435.
Lee et al., "Current strategies for pulmonary arterial hypertension," J. Internal Medicine, 2005, 258, 199-215.
Max et al., "Inhaled prostacyclin in the treatment of pulmonary hypertension," Eur. J. Pediatr., 1999, 158 Suppl 1, S23-S26.
McHugh, N. J., et al., "Infusion of Iloprost, a prostacyclin analogue, for treatment of Raynaud's phenomenon in systemic sclerosis", Annuals of the Rheumatic Diseases, vol. 47, No. 1, pp. 43-47 (1988).
McLaughlin et al., "Efficacy and Safety of Treprostinil: An Epoprostenol Analog for Primary Pulmonary Hypertension," Journal of Cardiovascular Pharmacology, Feb. 2003, 41(2):293-299.
Medterms.com (retrieved on Sep. 2, 2011: http://www.medterms.com/script/main/art.asp?articlekey=10001.
Mills, Sr., J. L., "Buerger's Disease in the $21^{st}$ Century: Diagnosis, Clinical Features, and Therapy", Seminars in Vascular Surgery, vol. 16, No. 3, pp. 179-189 (2003).
Mohler, III, E. R., et al., "Trial of a novel prostacyclin analog, UT-15, in patients with severe intermittent claudication", Vascular Medicine, vol. 5, pp. 231-237 (2000).
Mueller et al., "Potential therapeutic mechanisms of stable prostacyclin ($PGI_2$)-mimetics in severe peripheral vascular disease," Biomed. Biochim. Acta, 1988, 47(10/11):S40-S44.
Nizankowski et al., "Prostacyclin for Ischemic Ulcers in Peripheral Arterial Disease. A Random Assignment, Placebo Controlled Study," Thrombosis Research, 1985, 37:21-28.
Norgren et al,. "Inter-Society Consensus for the Management of Peripheral Arterial Disease (TASC II)," J. Vasc. Surg., Jan. 2007, S5A-S67A.
Norgren, L., et al., "A Stable Prostacycline Analogue (Iloprost) in the Treatment of Ischaemic Ulcers of the Lower Limb", Eur. J. Vasc. Surg., vol. 4, pp. 463-467 (1990).
O'Meara et al., "Systematic reviews of wound care management: (3) antimicrobial agents for chronic wounds; (4) diabetic foot ulceration," Health Technology Assessment, 2000, 4(21):15-228.
Olin, J. W., "Thromboangiitis Obliterans (Buerger's Disease)", The New Engl. J. Med., vol. 343, No. 12, pp. 864-869 (2000).
Olschewski et al. For the German PPH Study Group, "Inhaled iloprost to treat severe pulmonary hypertension—An uncontrolled trial," Annals of Internal Medicine, 2000, 132, 435-443.
Olschewski et al., Aerosolized prostacyclin and iloprost in severe pulmonary hypertension,: Annals of Internal Medicine, 1996, 124, 820 824.
Olschewski et al., "Inhaled prostacyclin and iloprost in severe pulmonary hypertension secondary to lung fibrosis," Am. Respir. Crit. Care Med., 1999, 160, 600-607.

(56) References Cited

OTHER PUBLICATIONS

Olschewski et al., "Pharmacodynamics and pharmacokinetics of inhaled iloprost, aerosolized by three different devices, in severe pulmonary hypertension," Chest, 2003, 124, 1294-1304.
Olschewski et al., "Prostacyclin and its analogues in the treatment of pulmonary hypertension," Pharmacology and Therapeutics, 2004, 102, 139-153.
Olschewski et al., "Recovery from circulatory shock in severe primary pulmonary hypertension (PPH) with aerosolization of iloprost," Intensive Care Med., 1998, 24, 631-634.
Osmonics Pure Water Handbook, $2^{nd}$ Edition, 1991, 151 pages.
Pappert et al., "Aerosolized Prostacyclin Versus Inhaled Nitric Oxide in Children with Severe Acute Respiratory Distress Syndrome," Anesthesiology, Jun. 1995, 82(6):1507-1511.
Patterson, J. H., et al., "Acute Hemodynamic Effects of the Prostacyclin Analog 15AU81 in Severe Congestive Heart Failure", The Amer. J. Card., vol. 75, pp. 26A-33A (1995).
Peckham et al., "Physiologic factors affecting pulmonary artery pressure in infants with persistent pulmonary hypertension," J. Pediatrics, 1978, 93(6):1005-1010.
Raychaudhuri, B., et al., "The Prostacyclin Analogue Treprostinil Blocks NF√B Nuclear Translocation in Human Alveolar Macrophages", J. Biol. Chem., vol. 277, No. 36, pp. 33344-33348 (2002).
Reeves, "Temperature-induced changes in blood acid-base status: pH and Pco2 in a binary buffer," Journal of Applied Physiology, 1976, 40(5):752-761.
Santak et al., "Prostacyclin aerosol in an infant with pulmonary hypertension," Eur. J. Pediatr., 1995, 154, 233-235.
Shigematsu et al,. "Factors affecting the long-term outcome of Buerger's disease (thromboangilitis obliterans)," International Angiology, Mar. 1999, 18(1):58-64, full article.
Shionoya, S., "Diagnostic criteria of Buerger's disease", Intl. J. Cardio. 66 (Suppl. 1), pp. S243-S245 (1998).
Simonneau et al., "Continuous Subcutaneous Infusion of Treprostinil, a Prostacyclin Analogue, in Patients with Pulmonary Arterial Hypertension," Am. J. Respir. Crit. Care Med., 2002, 165:800-804.
Soditt et al., "Improvement of oxygenation induced by aerosolized prostacyclin in a preterm infant with persistent pulmonary hypertension of the newborn," Intensive Care Med., 1997, 23, 1275-1278.
Steffen et al., "The Effects of 15AU81, a Chemically Stable Prostacyclin Analog, on the Cardiovascular and Renin-Angiotensis Systems of Anesthetized Dogs, Prostaglandins, Leukotrienes and Essential Fatty Acids," 1991, 43:277-286.
Stricker et al., "Sustained improvement of performance and haemodynamics with long-term aerosolized prostacyclin therapy in severe pulmonary hypertension," Schweiz Med. Wochenschr., 1999, 129, 923-927.
Tyle, P., "Iontophoretic Devices for Drug Delivery", Pharma. Res., vol. 3, No. 6, pp. 318-326 (1986).
Van Heerden et al., "Inhaled aerosolized prostacyclin as a selective pulmonary vasodilator for the treatment of severe hypertension," Anaesthesia and Intensive Care, 1996, 24, 87-90.
Van Heerden et al., "Re: Delivery of inhaled aerosolized prostacyclin (IAP)," Anaesthesia and Intensive Care, 1996, 24, 624-625.
Vippagunta et al., "Crystalline Solids," Advanced Drug Delivery Reviews, 2001, 48:3-26.
Voswinckel et al., "Acute effects of the combination of sildenafil and inhaled treprostinil on haemodynamics and gas exchange in pulmonary hypertension," Pulmonary Pharmacology & Therapeutics, 2008, 21, 824-832.
Voswinckel, R., Enke, B., Reichenberger, F., Kohstall, M., Kreckel, A., Krick, S., Gall, H., Gessler, T., Schmehl, T., Ghofrani, H.A., Schermuly, R.T., Grimminger, F., Rubin, L.J., Seeger, W. and Olschewski, H. Favorable effects of inhaled treprostinil in severe pulmonary hypertension. J. American College of Cardiology 2006, 48, 1672-1681.
Wade et al. "Effects of Continuous Subcutaneous Treprostinil Therapy on the Pharmacodynamics and Pharmacokinetics of Warfarin," Journal of Cardiovascular Pharmacology, Jun. 2003, 41(6):908-915.
Walmrath et al., "Effects of inhaled versus intravenous vasodilators in experimental pulmonary hypertension," Eur. Respir. J., 1997, 10, 1084-1092.
Wasserman et al., "Bronchodilator effects of prostacyclin (PGI2) in dogs and guinea pigs," European Journal of Pharmacology, 1980, 66, 53-63.
Webb et al., "The use of inhaled aerosolized prostacyclin (IAP) in the treatment of pulmonary hypertension secondary to pulmonary embolism," Intensive Care Med., 1996, 22, 353-355.
Wensel et al., "Effects of iloprost inhalation on exercise capacity and ventilator efficiency in patients with primary pulmonary hypertension," Circulation, 2000, 101, 2388-2392.
Wetzel, "Aerosolized Prostacyclin," Anesthesiology, 1995, 82(6).
Wetzel, R.C., "Aerosolized prostacyclin: in search of the ideal pulmonary vasodilator," Anesthesiology, 1995, 82, 1315-1317.
Wigley et al., "Intravenous iloprost treatment of Raynaud's phenomenon and ischemic ulcers secondary to systemic sclerosis," J. Rheumatol., Sep. 1992, 19(9):1407-1414, full article.
Zanen et al., "Optimal particle size for beta 2 agonist and anticholinergic aerosols in patients with severe airflow obstruction," Thorax, 1996, 51, 977-980.
Zanen et al., "The optimal particle size for β-adrenergic aerosols in mild asthmatics," International Journal of Pharmaceutics, 1994, 107, 211-217.
Zapol et al., "Pulmonary Circulation During Adult Respiratory Distress Syndrome," Pulmonary Cicculation During ARDS, 1985, 241-273.
Zwicke et al., "Treprostinil sodium for management of wounds refractory to standard therapy secondary to critical limb ischemia," Wounds, Mar. 2007, 19(3):A31.
Zwicke et al., "Treprostinil sodium for management of wounds refractory to standard therapy secondary to critical limb ischemia: an extension study," Wounds, Mar. 2007, 19(3):A32.

\* cited by examiner

Figure 1. Study design.

Figure 2. Disposition of patients enrolled.

Figure 3. Size of Target Lesions During Treprostinil Therapy

Figure 4. Average Improvement in Diameter of Baseline DIL

Figure 5: Number of Total and New DIL

Figure 6: Subjective Measures of DIL.

Figure 7. Resolution of target DIL overlying 3rd MCP

Figure 8. Mean and worst rest pain assessed by the patients.

Figure 12

● AEROSOL UT 15
○ INTRAVENOUS UT 15

Figure 14

- ● AEROSOL UT 15
- ○ INTRAVENOUS UT 15

PULMONARY ARTERIAL PRESSURE (cmH$_2$O)

BASELINE, UT 15 250 (ng/kg/min), UT 15 500 (ng/kg/min), UT 15 1000 (ng/kg/min)

INHALATION FORMULATIONS OF TREPROSTINIL

CROSS REFERENCE TO RELATED APPLICATIONS

The present application is a continuation of U.S. application Ser. No. 14/629,938, filed Feb. 24, 2015, which is a continuation of U.S. application Ser. No. 12/232,611, filed Sep. 19, 2008, which is abandoned and is a continuation in part of U.S. application Ser. No. 11/012,723 filed Dec. 16, 2004, which issued as U.S. Pat. No. 8,765,813, on Jul. 1, 2014, and claims priority to U.S. provisional application No. 60/529,622 filed Dec. 16, 2003, all of which are incorporated herein by reference in their entirety.

FIELD

The invention relates to the use of Treprostinil or its derivative, or a pharmaceutically acceptable salt thereof, to treat and/or prevent ischemic lesions, such as digital (fingers and toes) ulcers and necrotic lesions, caused by scleroderma, Buerger's disease, Raynaud's disease, Raynaud's phenomenon or other conditions. This invention also relates to kits to be used for this purpose.

BACKGROUND

Treprostinil, also known as UT-15, is a known compound disclosed in U.S. Pat. No. 4,306,075 in example 33. Treprostinil is a synthetic analog of epoprostenol, a prostaglandin $F_1$. The activities ascribed to the various compounds of this patent include inhibition of smooth muscle cell proliferation, inhibition of platelet aggregation, inhibition of cytokine secretion, reduction of gastric secretion, vasodilatation and bronchodilation.

U.S. Pat. No. 5,153,222 discloses the use of Treprostinil and related compounds to treat pulmonary hypertension. U.S. Pat. No. 6,054,486 discloses the use of Treprostinil and related compounds to treat peripheral vascular disease, such as peripheral arterial occlusive disease and intermittent claudication. Patterson et al., *Amer. J. of Cardiology*, 75: 26A-33A (1995), have shown vasodilator effects of Treprostinil in patients with class III or class IV heart failure.

Clapp et al., *Am. J. Respir. Cell. Mol. Biol.*, 26(2): 194-201 (2002), have shown that Treprostinil inhibits proliferation of human pulmonary arterial smooth muscle cells. Raychaudhuri et al., *J. Biol. Chem.*, 277(36): 33344-8 (2002), have disclosed that Treprostinil inhibits inflammatory cytokine (tumor necrosis factor-α, interleukin-1β, interleukin-6, and granulocyte macrophage colony-stimulating factor) secretion and gene expression by human alveolar macrophages.

Patients with diseases or conditions, such as scleroderma (including systemic sclerosis), experience, among other things, abnormalities in the blood vessels that supply the skin. As a result, these patients experience ulcerations or even areas of necrosis (tissue death) on certain parts of their skin. Ischemic lesions associated with diseases such as scleroderma tend to occur on the hands and fingers, often over the knuckles, but also on other bony prominences, such as elbows, knees, ankles and toes.

To date, the standard of care for treatment of ischemic lesions has included administration of topical hydrocolloid dressings, topical antibiotic ointments, analgesics for pain, debridement and wound care for ischemic wounds. Although certain types of dressings sometimes can help to aid healing of the lesions, the these treatments are often unsuccessful.

Other investigators have suggested that Ilomedin, a stable prostacyclin analog, may heal ischemic ulcers in lower limbs, as seen in patients with Buerger's disease. Fiessinger and Schafer, *Lancet*, 335(8689): 555-7 (1990); Norgren et al., *Eur. J Vasc. Surg.* (5): 463-7 (1990); Benthin, *Ugeskr Laeger*, 157(36): 4946-7 (1995). Others have suggested that patients treated with Ilomedin treatment may show improvements in the frequency and severity of Raynaud's attacks. Kyle et al., *J Rheumatol.*, (9): 1403-6 (1992); McHugh et al., *Ann Rheum Dis.*, 47(1): 43-7 (1988).

Mohler et al., *Vascular Medicine*, 5: 231-237 (2000) have demonstrated, in patients with severe intermittent claudication, that Treprostinil causes an increase in blood flow in large blood vessels of the lower limbs, such as the common femoral, superficial femoral, popliteal and anterial tibial arteries. These investigators also have found that Treprostinil stimulates detectable blood flow in ankles of certain peripheral arterial disease patients, who otherwise exhibited minimal or no detectable blood flow in the absence of treatment. Likewise, the investigators found that some patients show improved pulse volume recordings in lower limbs upon Treprostinil treatment.

Ischemic lesions, and particularly digital ischemic lesions, such as those caused by systemic schlerosis, are extremely painful, debilitating, and heal slowly. Thus, the need exists to identify viable methods, as well as kits, that can be used to prevent and treat such lesions. The present invention satisfies this need and provides related advantages as well.

SUMMARY

According to one embodiment, an inhalation formulation comprises a pharmaceutically effective amount of treprostinil sodium and a carrier suitable for administration with a nebulizer, wherein the formulation is in a solution form.

According to another embodiment, a method of treating pulmonary hypertension comprises administering by inhalation to a subject in need thereof an inhalation formulation comprising a pharmaceutically effective amount of treprostinil sodium and a carrier suitable for administration with a nebulizer, wherein the formulation is in a solution form.

According to yet another embodiment, administration of Treprostinil or its derivatives, or pharmaceutically acceptable salts thereof, reduces the occurrence, number, size and severity of ischemic lesions, including digital ischemic lesions (such as ulcers and necrotic lesions), present on subjects with diseases such scleroderma, Buerger's disease, Raynaud's disease, Raynaud's phenomenon, and other conditions. Treprostinil is well suited for the prevention and treatment of ischemic lesions, including digital ischemic lesions, because the compound is a stable analogue of prostaglandin, can be used in intravenous administration, is not degraded when it passes through the lungs, and has a long biological half-life.

Accordingly, present invention provides for the treatment or prevention of ischemic lesions, such as digital ischemic lesions, in subjects with scleroderma (including systemic schlerosis), Buerger's disease, Raynaud's disease, Raynaud's phenomenon, or other conditions, comprising administering to a subject in need thereof an effective amount of Treprostinil, its derivative or a pharmaceutically acceptable salt thereof. The present invention also provides for kits for accomplishing this purpose.

BRIEF DESCRIPTION OF THE FIGURES

FIG. 2 depicts the effects of the aerosolized UT15 administered to the sheep intravenously induced with U44069 on syst biological data relating to the use of such compounds. At column 59, example 31, the patent discloses a compound that is structurally similar to that of example 33 (UT-15), but it is not the same compound. Example 31 discloses (column 59, lines 41-45) that "[t]he compounds [sic] 9-deoxy-2',9α-methano-3-oxa-4,5,6-trinor-3,7-(1',3'-interphenylene)-PGF$_1$, methyl ester, given to a rat orally at a dose of 1 mg/kg lowered blood pressure 44 mmHg. After 52 min the blood pressure was still lower 14 mm." All blood is driven through the lungs via the pulmonary circulation in order, among other things, to replenish the oxygen which it dispenses in its passage around the rest of the body via the systemic circulation. The flow through both circulations is in normal circumstances equal, but the resistance offered to it in the pulmonary circulation is generally much less than that of the systemic circulation. When the resistance to pulmonary blood flow increases, the pressure in the circulation is greater for any particular flow. This is referred to as pulmonary hypertension. Generally, pulmonary hypertension is defined through observations of pressures above the normal range pertaining in the majority of people residing at the same altitude and engaged in similar activities.

Figure 1:
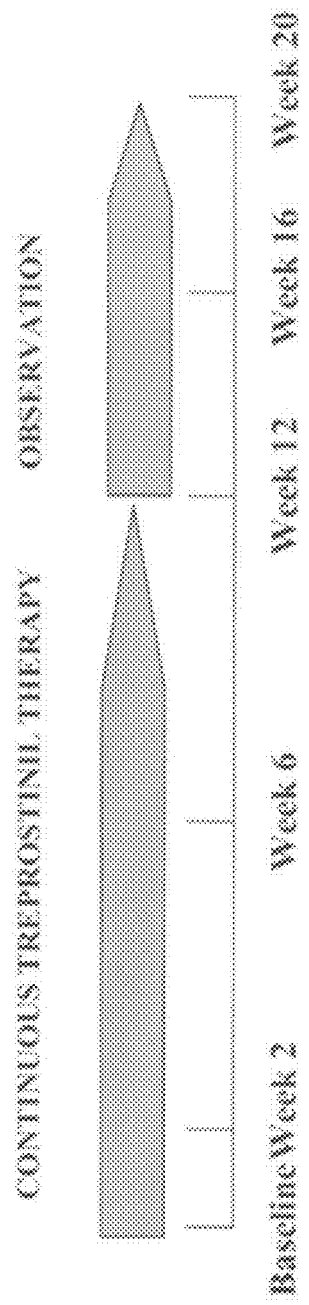
FIG. 1 shows the design of a study that examines the use of Treprostinil for the treatment and prevention of digital ischemic lesions in patients with systemic sclerosis.

Most often pulmonary hypertension is a manifestation of an obvious or explicable increase in resistance, such as obstruction to blood flow by pulmonary emboli, malfunction of the heart's valves or muscle in handling blood after its passage through the lungs, diminution in pulmonary vessel caliber as a reflex response to hypoventilation and low oxygenation, or a mismatch of vascular capacity and essential blood flow, such as shunting of blood in congenital abnormalities or surgical removal of lung tissue. Such pulmonary hypertension is referred to as secondary hypertension.

There remain some cases of pulmonary hypertension where the cause of the increased resistance is as yet inexplicable. They are described as primary pulmonary hypertension (PPH) and are diagnosed by and after exclusion of the causes of secondary pulmonary hypertension. Despite the possibility of a varied etiology, cases of primary pulmonary hypertension tend to comprise a recognizable entity. Approximately 65% are female and young adults are most commonly afflicted, though it has occurred in children and patients over 50. Life expectancy from the time of diagnosis is short, about 3 to 5 years, though occasional reports of spontaneous remission and longer survival are to be expected given the nature of the diagnostic process. Generally, however, progress is inexorable via syncope and right heart failure and death is quite often sudden. Pulmonary hypertension refers to a condition associated with an elevation of pulmonary arterial pressure (PAP) over normal levels. In humans, a typical mean PAP is approximately 12-15 mm Hg. Pulmonary hypertension, on the other hand, is sometimes marked by PAP increases by at least 5 to 10 mm Hg over normal levels. PAP readings as high as 50 to 100 mm Hg over normal levels have been reported. When the PAP markedly increases, plasma can escape from the capillaries into the lung interstitium and alveoli. Fluid buildup in the lung (pulmonary edema) can result, with an associated decrease in lung function that can in some cases be fatal. Pulmonary hypertension may either be acute or chronic. Acute pulmonary hypertension is often a potentially reversible phenomenon generally attributable to constriction of the smooth muscle of the pulmonary blood vessels, which may be triggered by such conditions as hypoxia (as in high-altitude sickness), acidosis, inflammation, or pulmonary embolism. Chronic pulmonary hypertension is characterized by major structural changes in the pulmonary vasculature, which result in a decreased cross-sectional area of the pulmonary blood vessels. This may be caused by, for example, chronic hypoxia, thromboembolism, or unknown causes (idiopathic or primary pulmonary hypertension). Pulmonary hypertension has been implicated in several life-threatening clinical conditions, such as adult respiratory distress syndrome ("ARDS") and persistent pulmonary hypertension of the newborn ("PPHN"). Zapol et al., Acute Respiratory Failure, p. 241-273, Marcel Dekker, New York (1985); Peckham, J. Ped. 93:1005 (1978). PPHN, a disorder that primarily affects full-term infants, is characterized by elevated pulmonary vascular resistance, pulmonary arterial hypertension, and right-to-left shunting of blood through the patent ductus arteriosus and foramen ovale of the newborn's heart. Mortality rates range from 12-50%. Fox, Pediatrics 59:205 (1977); Dworetz, Pediatrics 84:1 (1989). Pulmonary hypertension may also result in a potentially fatal heart condition known as "cor pulmonale", or pulmonary heart disease. Fishman, "Pulmonary Diseases and Disorders" 2$^{nd}$ Ed., McGraw-Hill, New York (1988).

The treatment of pulmonary hypertension by the parenteral administration of certain prostaglandin endoperoxides, such as prostacyclin (also known as flolan), is also known and is the subject of U.S. Pat. No. 4,883,812. Prostacyclin has been administered by inhalation and is used to treat pulmonary hypertension by inhalation. Anesthesiology, vol. 82, no. 6, pp. 1315-1317.

This invention relates to the administration of a therapeutically effective amount of a benzindine prostaglandin to a mammal in need thereof by inhalation. More particularly, the invention relates to a method of treating pulmonary hypertension by administering an effective amount of a benzindine prostaglandin to a mammal in need thereof by inhalation.

Inhalation of benzindine prostaglandins provides unexpectedly superior results compared to parenteral administration of benzindene prostaglandins.

Unless otherwise specified, all references to "a" or "an" mean at least one.

One embodiment of the present invention is a method of delivering a benzindene prostaglandin or a pharmaceutically acceptable salt or ester thereof to a mammal in need thereof by inhalation.

A preferred group of benzindene prostaglandins for delivery by inhalation according to the present invention is as follows:

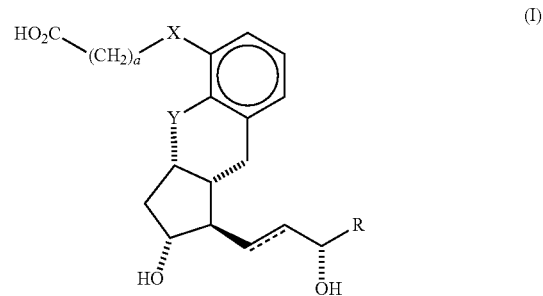

wherein a is an integer of from 1 to 3; X and Y, which may be the same or different, are selected from —O— and —CH2-; R is —(CH2)5-R1 wherein R1 is hydrogen or methyl, or R is cyclohexyl, or R is —CH(CH3)

CH2C≡CCH3; and the dotted line represents an optional double bond; or a physiologically acceptable salt or acid derivative thereof.

The most preferred benzindene prostaglandin is UT-15, which is 9-deoxy-2',9-alpha-methano-3-oxa-4,5,6-trinor-3,7-(1',3-interphenylene)-13,14-dihydro-prostaglandin F1. "Inhalation" delivery in the context of this invention refers to the delivery of the active ingredient or combination of active ingredients through a respiratory passage, wherein the mammal in need of the active ingredient(s) inhales the active ingredient(s) through the mammal's airways, such as the nose or mouth.

Active ingredients, which are aerosolized, atomized, and/or nebulized for delivery by inhalation according to the present invention include liquid formulations comprising a benzindene prostaglandin, such as UT-15, alone or in combination with other active ingredients described below. UT-15 may be used as a free acid or in the form of a pharmaceutically acceptable salt or ester or other acid derivative. In addition, sustained release formulations comprising UT-15 may be used, including PEGylated forms and/or protein-conjugated forms of UT-15.

The term "acid derivative" is used herein to describe C1-4 alkyl esters and amides, including amides wherein the nitrogen is optionally substituted by one or two C1-4 alkyl groups.

The invention also includes bioprecursors or "pro-drugs" of UT-15, that is, compounds which are converted in vivo to UT-15 or its pharmaceutically active derivatives thereof.

Further aspects of the present invention are concerned with the use of UT-15, or a pharmaceutically acceptable salt or acid derivative thereof, in the manufacture of a medicament for the treatment of peripheral vascular disease The present invention extends to non-physiologically acceptable salts of UT-15 which may be used in the preparation of the pharmacologically active compounds of the invention. The physiologically acceptable salts of UT-15 include salts derived from bases.

Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

Optionally, one or more pharmaceutically acceptable carriers or excipients may be included in the formulation to be aerosolized, atomized, or nebulized according to the invention.

A preferred solution for administration by inhalation with a nebulizer includes a sterile solution of UT-15 comprising UT-15, sodium citrate, citric acid, sodium hydroxide, sodium chloride, and meta-cresol. A more preferred solution is prepared by mixing 0.125 grams UT-15, 1.25 grams hydrous sodium citrate, 0.125 grams of anhydrous citric acid, 0.05 grams of sodium hydroxide, and approximately 250 ml of water for injection.

Preferably, a nebulizer, inhaler, atomizer or aerosolizer is used which forms droplets from a solution or liquid containing the active ingredient(s). The droplets are preferably less than 10 micrometers in diameter. One preferred nebulizer is the AM-601 MEDICATOR AEROSOL DELIVERY SYSTEM™ (a nebulizer manufactured by Healthline Medical in Baldwin Park, Calif.).

Alternatively, solid formulations, usually in the form of a powder, may be inhaled in accordance with the present invention. In such case, the particles are preferably less than 10 micrometers in diameter, and more preferably, less than 5 micrometers in diameter.

This invention further relates to delivering a benzindene prostaglandin and/or its salts pr esters by inhalation for applications where inhalation delivery is appropriate for the treatment of that particular condition. Benzindene prostaglandins, including UT-15 and its salts or esters, have been shown to be useful for multiple applications. For example, UT-15 has been shown to exhibit a potent anti-aggregatory action on blood platelets, and therefore has a particular utility in mammals as an anti-thrombotic agent. Further known uses of UT-15 include treatment of peripheral vascular disease (covered in co-pending application Ser. No. 09/190,450, the entire contents of which are incorporated by reference herein). In the case of treating peripheral vascular disease by inhalation of a benzindene prostaglandin of the present invention, the dosage for inhalation, taking into account that some of the active ingredient is breathed out and not taken into the bloodstream, should be sufficient to deliver an amount that is equivalent to a daily infusion dose in the range of 25 μg to 250 mg; typically from 0.5 μg to 2.5 mg, preferably from 7 μg to 285 μg, per day per kilogram bodyweight. For example, an intravenous dose in the range 0.5 μg to 1.5 mg per kilogram bodyweight per day may conveniently be administered as an infusion of from 0.5 ng to 1.0 μg per kilogram bodyweight per minute. A preferred dosage is 10 ng/kg/min.

Benzindene prostaglandins, including UT-15 and its salts or esters, may also be administered according to the present invention by inhalation to reduce and control excessive gastric secretion, thereby reducing or avoiding gastrointestinal ulcer formation, and accelerating the healing of ulcers and lesions already present in the gastrointestinal tract. In addition, benzindene prostaglandins may also be administered according to the present invention by inhalation to treat congestive heart failure, to reduce inflammation and/or pulmonary hypertension associated with lung transplants.

Benzindene prostaglandins, including UT-15 and its salts or esters, further exhibit vasodilatory action on blood vessels and therefore have a particular utility as anti-hypertensives for the treatment of high blood pressure in mammals, including man. Use as an anti-hypertensive (or hypotensive agent) may be accomplished by administering a pharmaceutical composition containing a benzidene prostaglandin, including UT-15.

Benzindene prostaglandins, including UT-15, may be used according to the present invention by inhalation to treat any condition where it is desired to reduce blood pressure, inhibit platelet aggregation, to reduce the adhesive character of platelets, and/or to treat or prevent the formation of thrombi in mammals, including man. For example, they may be used in the treatment and prevention of myocardial infarcts and in the treatment of peripheral vascular disease, to treat and prevent post-operative thrombosis, to promote patency of vascular grafts following surgery, and to treat complications of arteriosclerosis and conditions such as atherosclerosis, blood clotting defects due to lipemia, and other clinical conditions in which the underlying etiology is associated with lipid imbalance or hyperlipidemia. Moreover, benzindene prostaglandins, including UT-15 and its salts or esters, have a further utility in the promotion of wound healing in mammals, including man.

Benzindene prostaglandins, including UT-15 and its salts or esters, may also be used as additives to blood, blood products, blood substitutes, and other fluids, which are used in artificial extra-corporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of UT-15. For this purpose, UT-15 or its salts or esters may be introduced by inhalation until it reaches a level in the circulating blood, the blood of the donor animal, or the blood of the perfused body portion, or to two or all of those equivalent to a steady state dose of 0.001 micrograms to 10 micrograms, per liter of circulating fluid. Another embodiment is to use UT-15 in laboratory animals, e.g., cats, dogs, rabbits, monkeys and rats, for these purposes in order to develop new methods and techniques for organ and limb transplants.

In accordance with the present invention, a benzindine prostaglandin is delivered by inhalation to a patient in need thereof in a "therapeutically effective amount". A "therapeutically effective amount" refers to that amount that has therapeutic effects on the condition intended to be treated or prevented. For example, an "antihypertensive effective amount" refers to that amount in which the effects from pulmonary hypertension, and particularly, pulmonary arterial pressure (PAP), are reduced towards a normal level relative to hypertensive levels, or maintained at normal levels. The precise amount that is considered effective for a particular therapeutic purpose will, of course, depend upon the specific circumstances of the patient being treated and the magnitude of effect desired by the patient's doctor. Titration to effect may be used to determine proper dosage.

Such formulations, both for veterinary and for human medical use, of the present invention comprise the active ingredient, a benzindene prostaglandin or salt or ester thereof, together with one or more pharmacologically acceptable carriers therefor and optionally other therapeutic ingredients. The carrier(s) must be "acceptable" in the sense of being compatible with the other ingredients of the formulation and not deleterious to the recipient thereof.

Furthermore, the formulations may conveniently be presented in unit dosage form and may be prepared by any of the methods well known in the art of pharmacy. All methods include the step of bringing into association the active ingredient with the carrier which constitutes one or more pharmacologically acceptable accessory ingredients.

The invention further relates to a method of treating pulmonary hypertension by inhalation of a benzindene prostaglandin. "Pulmonary hypertension" refers to both acute and chronic hypertension, including primary pulmonary hypertension and secondary pulmonary hypertension, and is associated with an elevated pulmonary arterial pressure over normal levels.

The efficacy of benzindene prostaglandins, such as UT-15, for treating pulmonary hypertension can be assessed by determining the hemodynamics associated with pulmonary hypertension. In particular, measurements of pulmonary arterial pressure (PPA), left atrial pressure (PLA), central venous pressure (PCV), systemic arterial pressure (PSYS), heart rate (HR), and cardiac output (CO) are useful in determining the effects of benzindene prostaglandins delivered by inhalation or parenterally.

Although pulmonary arterial pressure can be directly measured and is often used to quantify pulmonary arterial hypertension, PPA can be affected by 3 other variables: CO, PLA and PVR, as indicated by Equation 1:

$$PPA=(CO*PVR)+PLA \qquad (1)$$

As can be seen from Equation 1, PPA can be elevated by increases in PLA (e.g., left heart failure, mitral valve stenosis, mitral valve regurgitation), increases in CO (e.g., low hematocrit, peripheral vasodilation, left to right shunt, etc.), and by increases in PVR (decreased pulmonary vascular surface area, decreased pulmonary vascular radii, pulmonary vascular obstructions, etc.).

On the other hand, PVR can not be directly measured and must be calculated by the following Equation 2:

$$PVR=(PPA-PLA)/CO \qquad (2)$$

PVR is a better index of pulmonary arterial hypertension (PAH), since interventions used to treat PAH are best if they only affect PVR and have no or little effect on CO and PLA.

Heart rate was determined by measuring the time (seconds) required for 25 heart beats to occur (t25) as indicated by the pulsations on the blood flow meter; the beats per minute (BPM) were calculated by the following equation:

$$BPM=(25 \text{ beats}/t25)*60 \text{ seconds}$$

All pressure may be monitored by commercially available transducers, such as Model 1290A HEWLETT PACKARD™ transducer (Andover, Mass.), which is attached to VALIDYNE CD19A Carrier Dmod. Amplifiers (Northridge, Calif.). Cardiac output may be measured by a Transonic Systems T101 Ultrasonic Bloodflow Meter (Ithaca, N.Y.). The pressure and blood flow signals may be recorded on ASTROMED MT-9500 Stripchart Recorder (West Warwick, R.I.) and digitally recorded with a personal computer using Easy Data Acquisition Software (Nashville, Tenn.).

It has been discovered that aerosolized UT-15 has both greater potency and efficacy relative to attenuating chemically induced pulmonary hypertension as shown by an increase in pulmonary vascular resistance. Furthermore, aerosolized UT-15 has a greater potency as compared to intravascularly administered UT-15, since the actual amount of UT-15 delivered via aerosolization delivery is only a fraction (10-50%) of the dosage delivered intravascularly. While the mechanism(s) that accounts for the greater potency and efficacy for aerosolized UT-15 is unknown, it can be hypothesized that a low "first-pass" uptake via intravenous infusion of UT-15 could be at least partially responsible. A low first-pass uptake would thus allow the majority of the drug to be made available to the peripheral circulation (including the coronary circulation), which would increase the heart rate and cardiac output. Aerosolized UT-15 has no apparent peripheral effects, such as on the heart rate or cardiac output, as compared to intravascular UT-15 during pulmonary vascular hypertension by chemical inducement. This is particularly beneficial for those patients that are near right heart failure and where peripheral vasodilation would exacerbate the challenge to the right heart. On the other hand, if cardiac output is compromised due to right heart failure, then aerosolized prostaglandin would decrease PVR and could allow cardiac output to increase while allowing lowering the load upon the right heart.

The following examples are provided by way of an illustration of the present invention and should in no way be construed as constituting a limitation thereof.

EXAMPLES

Example I

Animal Model

Inhalation solutions were prepared by combining 1.25 grams of Sodium Citrate (Hydrous), 0.125 Citric Acid (Anhydrous), 0.05 grams of Sodium Hydroxide (NF/BP), 0.125 grams of UT-15, and approximately 250 ml of Water for Injection according to the following steps.
1. Measured approximately 210 ml of water into a sterile siliconized glass beaker with a magnetic stir bar
2. Added sodium citrate. Mixed until dissolved.
3. Added citric acid to Step 2 solution. Mixed until dissolved.
4. Measured 12.5 ml of water into sterile plastic tube. Added sodium hydroxide. Mixed until dissolved.
5. Added UT15 to Step 4 solution. Mixed by hand until dissolved.
6. Added the Step 5 solution to Step 3 solution and mixed.
7. pH was adjusted using hydrochloric acid and/or sodium hydroxide solutions to a value of 7.3
8. Final solution was filtered using sterile microfilter into another sterile beaker, then 5 ml of solution was aliquoted to sterile stoppered blood test tubes.
9. Solutions were double boxed and put in −4 degrees Celsius freezer.
10. Placebo solution made up as described above except UT-15 not added and quantities adjusted to make only 50 ml.

Working solution was made by adding sterile saline to dilute the UT15 stock solution or placebo to the desired amount (depending on dose desired, weight of sheep, and duration of aerosolizing). This solution was then added to the nebulizer in volumes not exceeding 5 ml until entire amount was used.

For a 35 kg sheep at a UT-15 dose of 250 ng per kg per minute for 30 minutes, the calculations used were, Calculations: 250×35×30=262,500 ng of UT-15 or 262.5 micrograms of UT-15. The nebulization rate was 0.28 ml per minute, thus 8.4 ml of solution was needed containing 262.5 micrograms of UT-15. However, an amount of solution is needed for the "void" volume (volume always left in the nubulizer). Thus a volume of 9 ml containing a total of 281.25 micrograms of UT-15 (or 0.5625 ml of the stock solution) was made up.

0.5625 ml of UT-15 was measured and added to 8.4375 of sterile saline. This was nebulized over exactly 30 minutes.

Sheep were used as the animal model of choice for these experiments for a number of reasons. First is the docile nature of sheep. They will stand quietly in metabolic cages without having to utilize tranquilizing drugs, which have the potential to complicate experimental results. Second, sheep are large enough to allow direct measurement of CO, PPA, PLA, PCV, and PSYS. Sheep are also large enough to allow direct aerosolization of substances into the lung via tracheostomy thereby preventing swallowing of drugs and thus eliminating a possible secondary route of administration of UT-15. Third, sheep can tolerate a great amount of instrumentation with little or no discomfort. Fourth, sheep have been utilized for several years as an animal model of pulmonary arterial hypertension and thus, there is a great amount of historical data with which to compare the results. The agent chosen to induce pulmonary arterial hypertension was a PGH2 analog, U44069 (9,11-dideoxy,9α,11α-epoxymethanoprostaglandin $F_{2\alpha}$). The reasons for using U44069 are that it is a very potent pulmonary vasoconstrictor, its characteristics are very similar to endogenously formed thromboxane A2, and it can be titrated to induce the desired degree of pulmonary vasoconstriction. U44069 was mixed with sterile normal saline immediately prior to being used and was protected from light by wrapping the solution with aluminum foil. The concentration of U44069 was adjusted such that a minimal flow rate of 0.8 ml per min was being infused into the sheep. This was done because more concentrated U44069 would have to be infused at very low rates and often causes "pulses" of U44069 due to the infusion characteristics of roller pumps. The U44069 pulses cause vasoconstriction "spikes" and thus would create induce a non-steady-state.

Surgical Procedures

Six yearling sheep (3 males, 3 females; 21-37 kg) were fasted 18-24 hours and initially anesthetized with a short acting barbiturate (thiopental) to allow intubation of the sheep. Halothane gas anesthesia (1.5-2.5%) was then used for the surgical procedures. Via a left thoracotomy, a Transonic blood flow probe was placed around the main pulmonary artery, silastic catheters placed in the main pulmonary artery and left atrium. After approximately 7 days the sheep were reanesthetized and the left carotid artery cannulated, a Cordis Introducer Sheath inserted in the left jugular vein, and a tracheotomy made. The sheep were allowed to recover for another 3-5 days prior to experimentation. These sheep were used to allow measurement of pulmonary arterial pressure (PPA), left atrial pressure (PLA), central venous pressure (PCV), systemic arterial pressure (PSYS), heart rate (HR), and cardiac output (CO) after baseline measurements were made for a minimum of 30 minutes.

Example II

Effects of Prolonged U44069 Intravenous Infusion on Pulmonary Vascular Resistance In four sheep, the ability of U44069 to maintain a steady-state increase in PVR was determined. After a 30 minute baseline, U44069 was infused at a rate of 1 microgram per kg of body weight per minute for 180 minutes. As can be seen by FIG. 1, the increase in PVR induced by intravenously induced U44069 is very stable over 3 hours. (In the figures, all data are given as mean±SEM. "*" indicates significantly different from corresponding intravenously infusion UT-15 delivery rate. "#" indicates significantly different from corresponding baseline value. "&" indicates significantly different from corresponding U44069 value.) Statistical analysis was also tested using multiple paired t-tests, which are not as rigorous as One-way ANOVA/Dunnett's test. In particular, FIG. 9 illustrates that intravenously infused U44069 causes PVR to reach a steady-state increase by 30 minutes and that the steady-state increase lasts for a minimum of 180 minutes. U44069 caused significant alterations in other variables (data not shown) over the 180 minute infusion period relative to their baseline values: PPA increased, HR decreased, CO decreased. PSYS increased above baseline values, however, the differences were not statistically different except at 120, 150 and 180 minutes during U44069 infusion. PCV also increased during U44069 infusion, however, the increases were only significant at 30 and 60 minutes. PLA did not significantly change at any of the time points investigated.

Since all of the U44069 time values were different from baseline yet none were different from each other as determined by the paired t-tests, this would argue strongly that there were no differences at any of the time points during U44069 infusion. These data would indicate that any alterations in PVR by UT-15 is due to the effects of UT-15 and not complicated by waning of the vasoconstrictor response.

Example III

Effects of Aerosolized UT-15 Given at High Doses on Baseline Hemodynamics

Baseline measurements consisted of 30 minutes of monitoring during vehicle/saline aerosolization (0.28 ml/min). After baseline measurements, the vehicle/saline solution in the aerosol delivery system was replaced with the stock UT-15 solution (500 ng/ml) and was aerosolized at 0.28 ml/min for 90 minutes.

Figure 10:
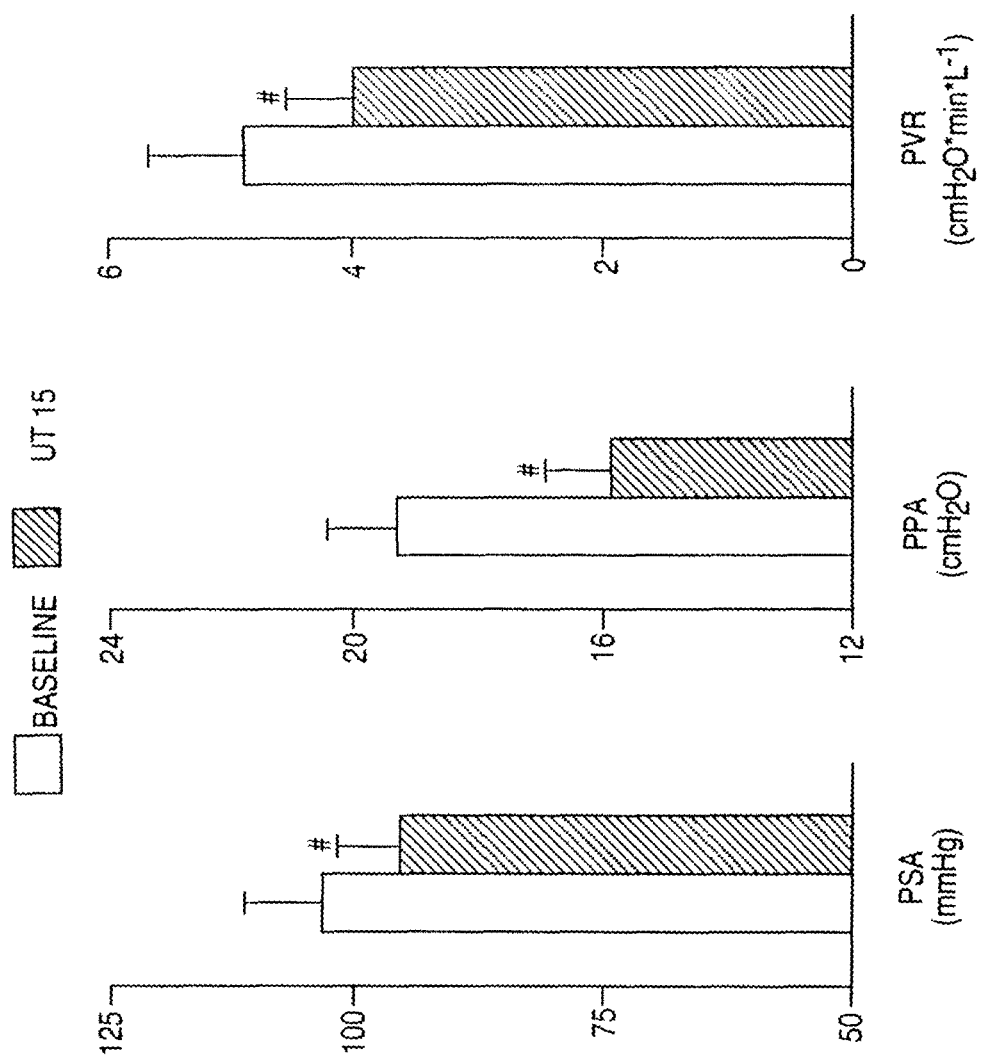
FIG. 10 describes the effects of a high dose of UT15, given as an aerosol, on the hemodynamic variables of the sheep. Specifically.

FIG. 10 depicts the only statistically altered variables observed after 90 minutes of high dose aerosolized UT-15 (3800-5700 ng per kg per min). PSYS decreased by 7.5%, PPA decreased by approximately 18%, and PVR decreased by approximately 19% relative to their respective baseline values.

These data are important in that this would indicate that, unlike intravenously infused UT-15, aerosolized UT-15 can be given in high doses without significant non-lung effects, i.e., heart rate, cardiac output. The aerosol delivery of UT-15 for these experiments is approximately 15-27 times that of the effective minimal tested dose of 250 ng per kg per min shown in FIG. 24.

Example IV

Control Intravenous UT-15 and Control Aerosolized UT-15 Dose Response Effects on Baseline Hemodynamics Two separate experiments were conducted to determine the dose response effects of intravenously infused UT-15 on baseline hemodynamics and aerosolized UT-15 on baseline hemodynamics. For the infusion experimental protocol, after a 30 minute baseline was established, UT-15 was infused intravenously at 3 rates (250, 500 and 1000 ng per kg per min). In three sheep, the infusion rates lasted for 30 minutes each, and for the other three sheep, the infusions were for 60 minutes each.

The aerosolized UT-15 protocol involved establishing a 30 minute baseline, then administering aerosolized UT-15 via a tracheostromy at rates of 250, 500 and 1000 microgram per kg of body weight per min and at an aerosolization rate of 0.28 ml/min. Again, three sheep were aerosolized for 30 minutes and the other three sheep were aerosolized for 60 minutes.

Figure 11:
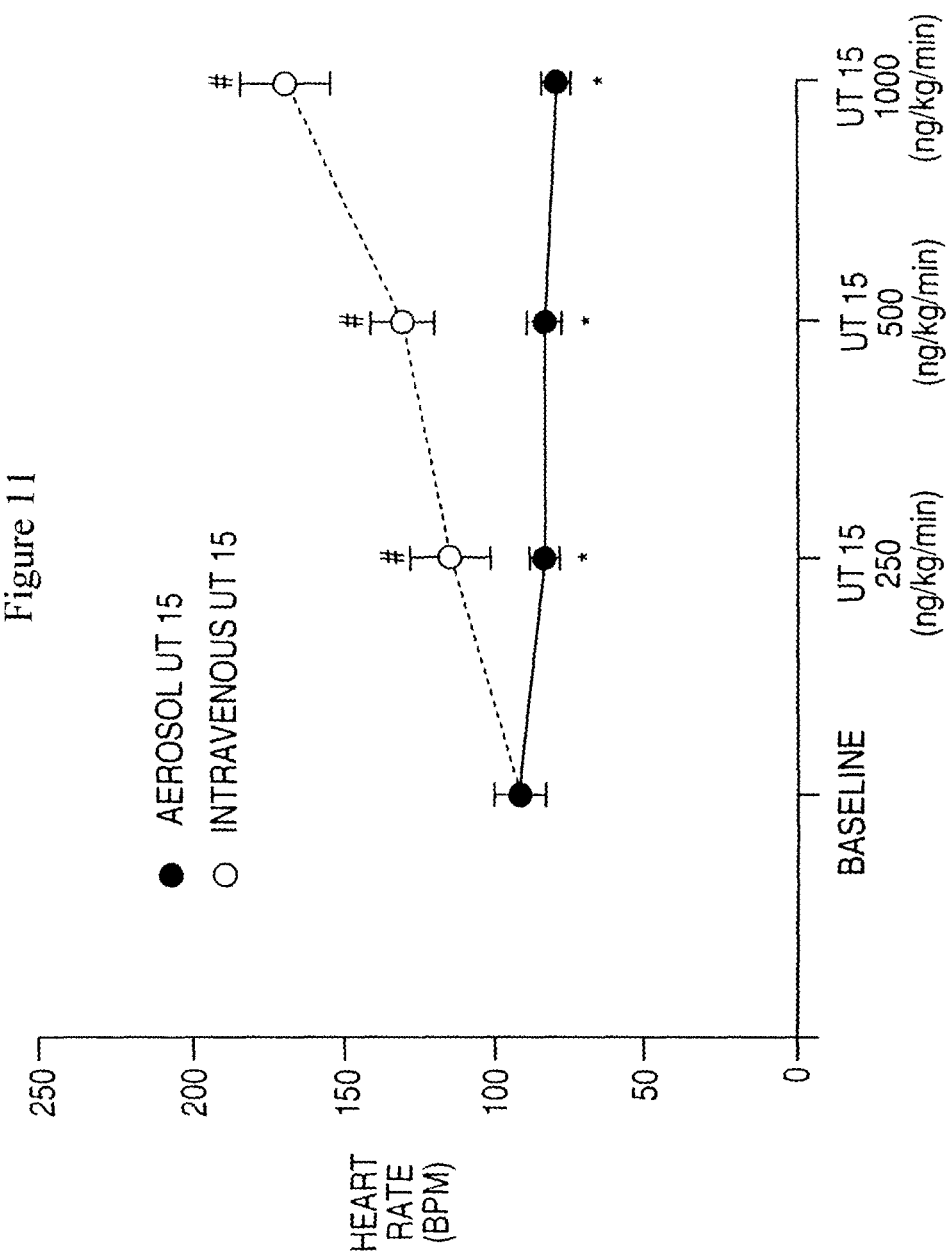

No differences were found between 30 minute and 60 minute UT-15 delivery at each of the 3 rates of administration. FIG. 11 shows the dose-response of intravenously infused and aerosolized UT-15 on heart rate. Heart rate significantly increased during intravenous administration of UT-15 at 250, 500 and 1000 ng per kg per min. Aerosolized UT15 had no effect on heart rate. There was a significant difference between aerosolized and intravenously infused UT-15 at each of the 3 rates of administration.

Figure 12:
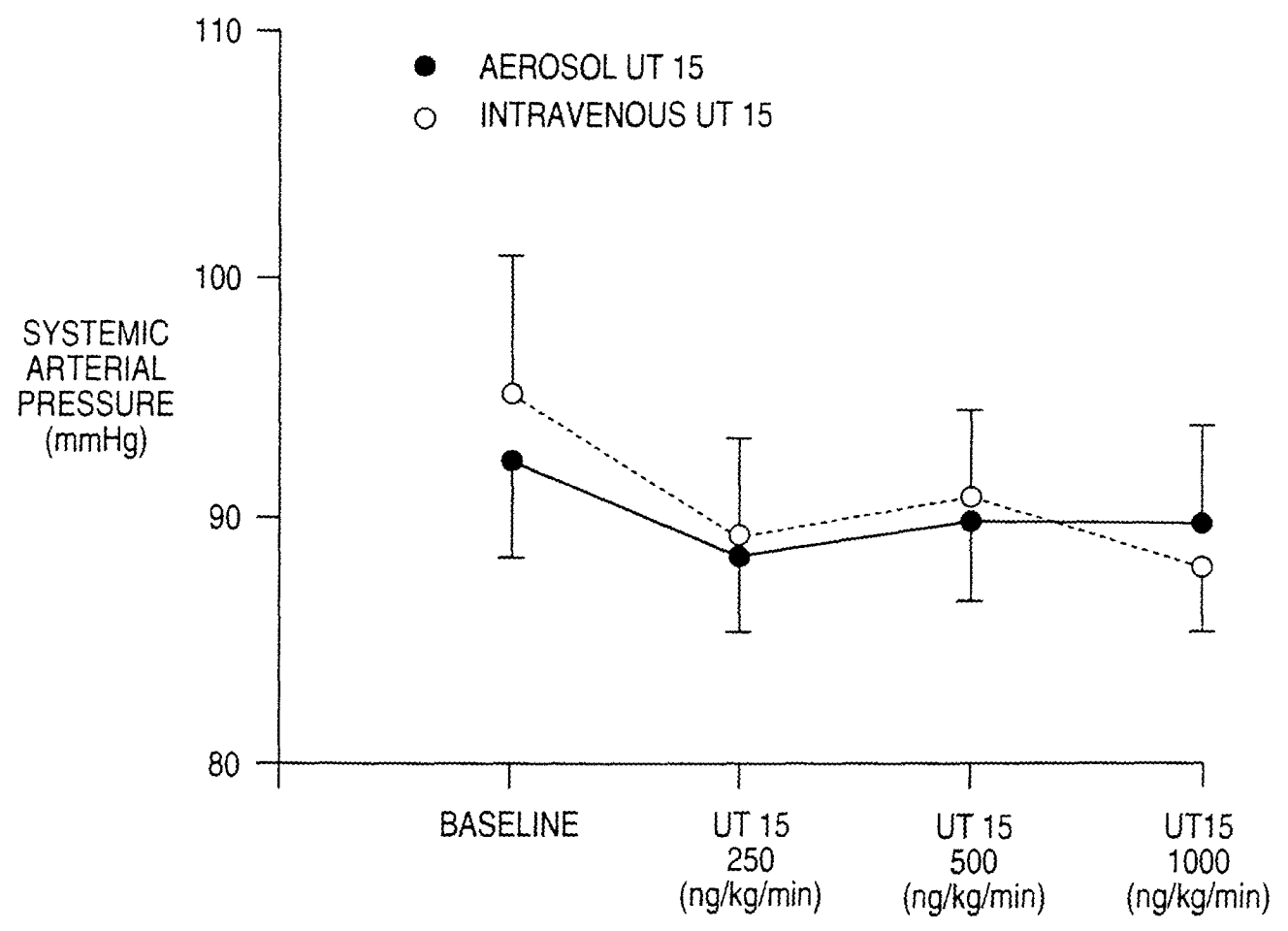

FIG. 12 shows that both aerosolized and intravenous UT-15 had no significant effect on PSYS at any of the administration rates used.

Figure 13:
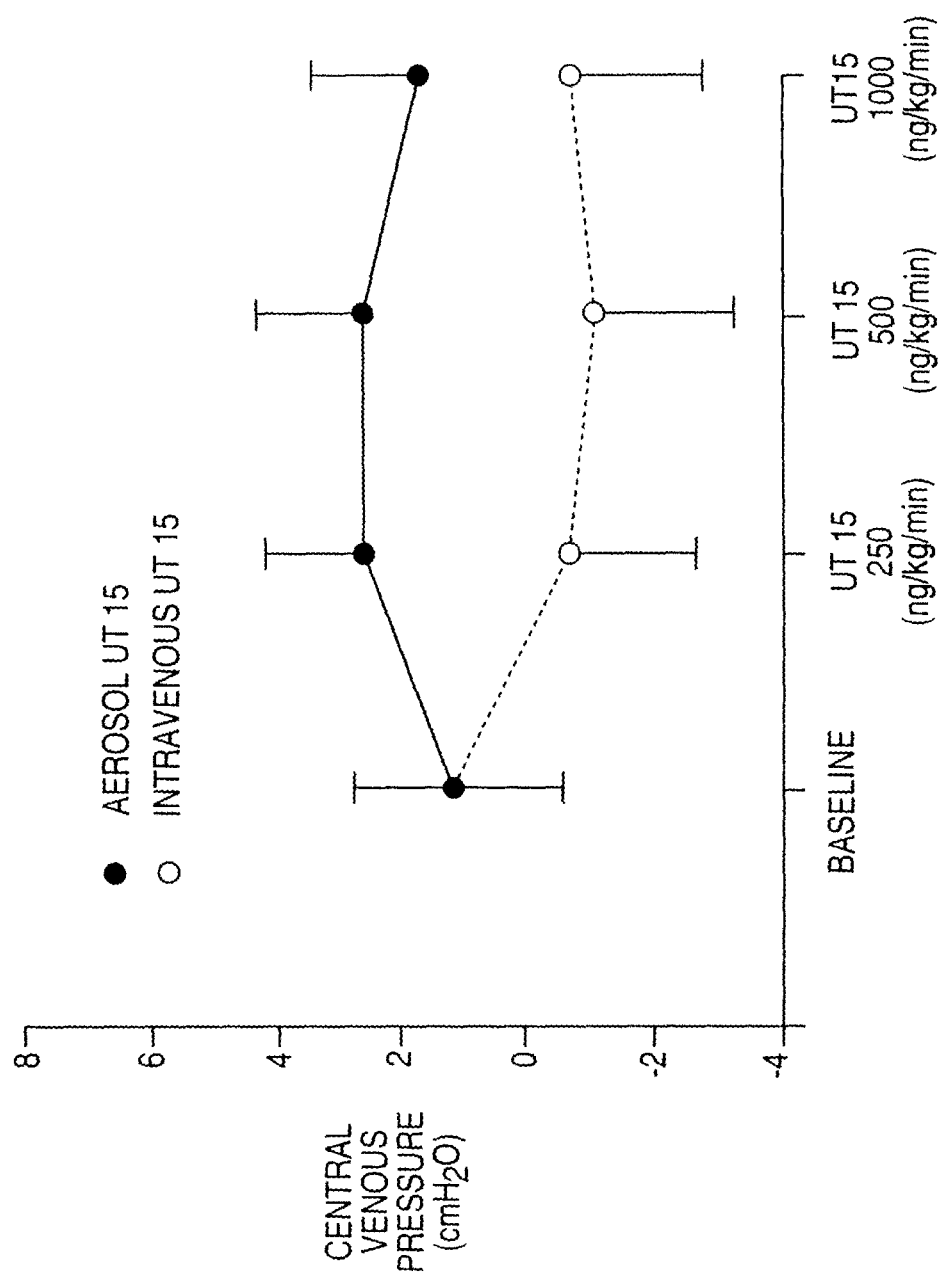
Figure 18:
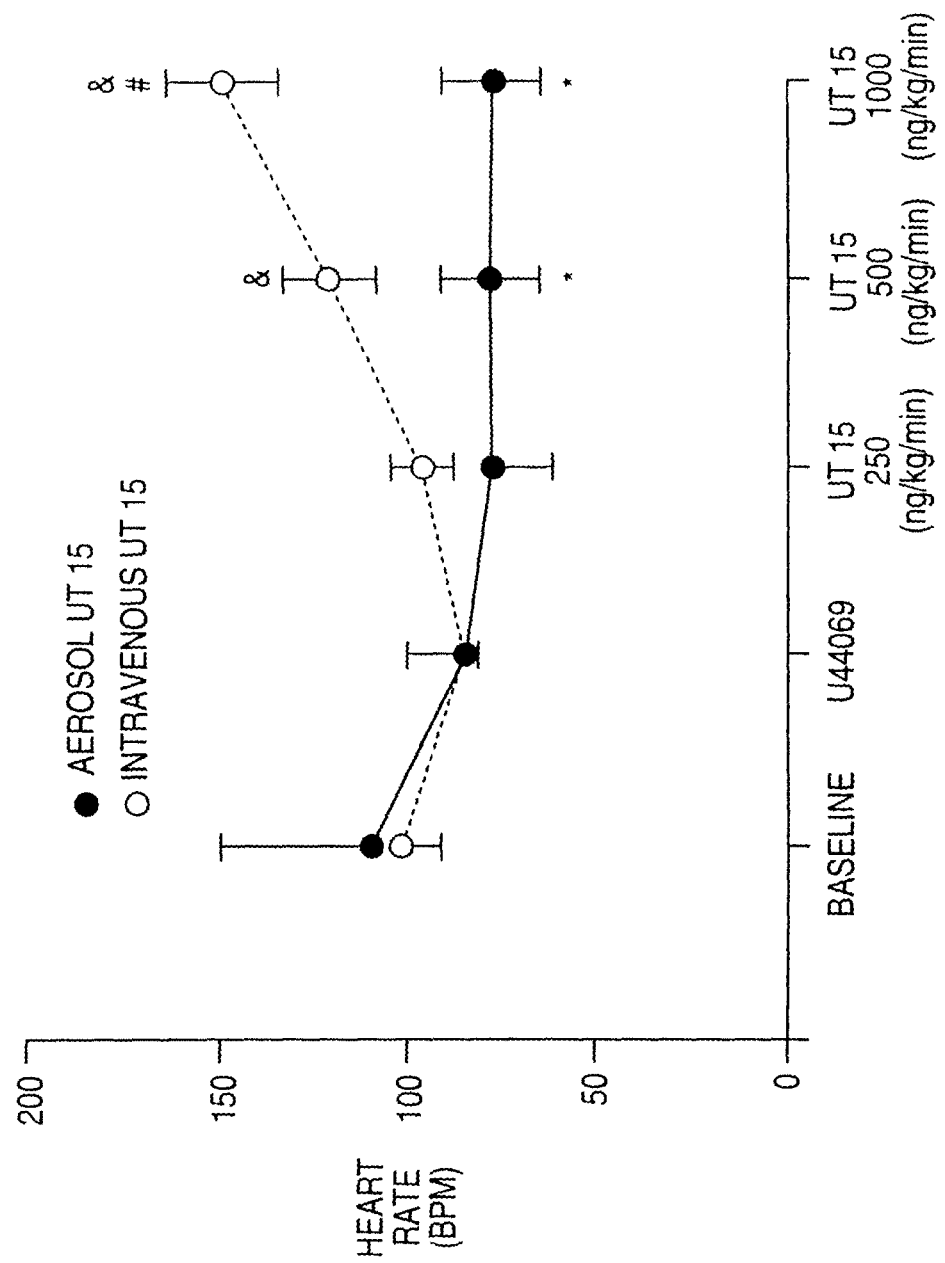

The effects of UT-15 on PCV are depicted by FIG. 13. There were no statistical difference at any dose relative to its baseline value nor between intravenous and aerosol administered UT-15 at any respective dose. The same effects were also observed for PPA as indicated by FIG. 14, although there was a general trend for PPA to decrease when UT-15 was aerosolized.

Figure 15:
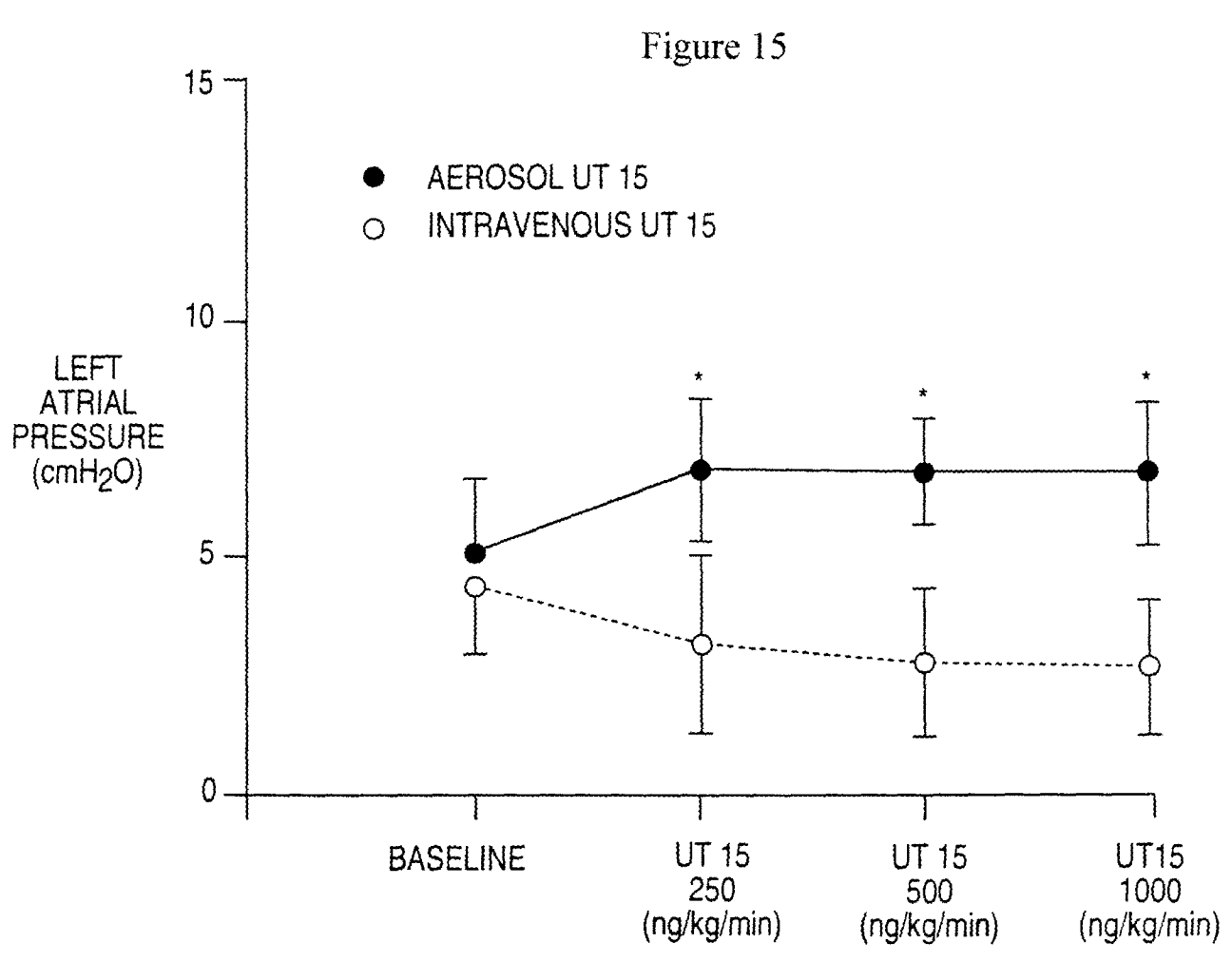

Interestingly, while neither intravenous nor aerosolized UT-15 caused PLA to significantly change from their respective baselines (although the mean values increased during aerosol delivery and decreased for intravenous delivery), there were significant differences between aerosolized and intravenous administered UT-15 at each of the delivery rates. See FIG. 15.

Figure 16:
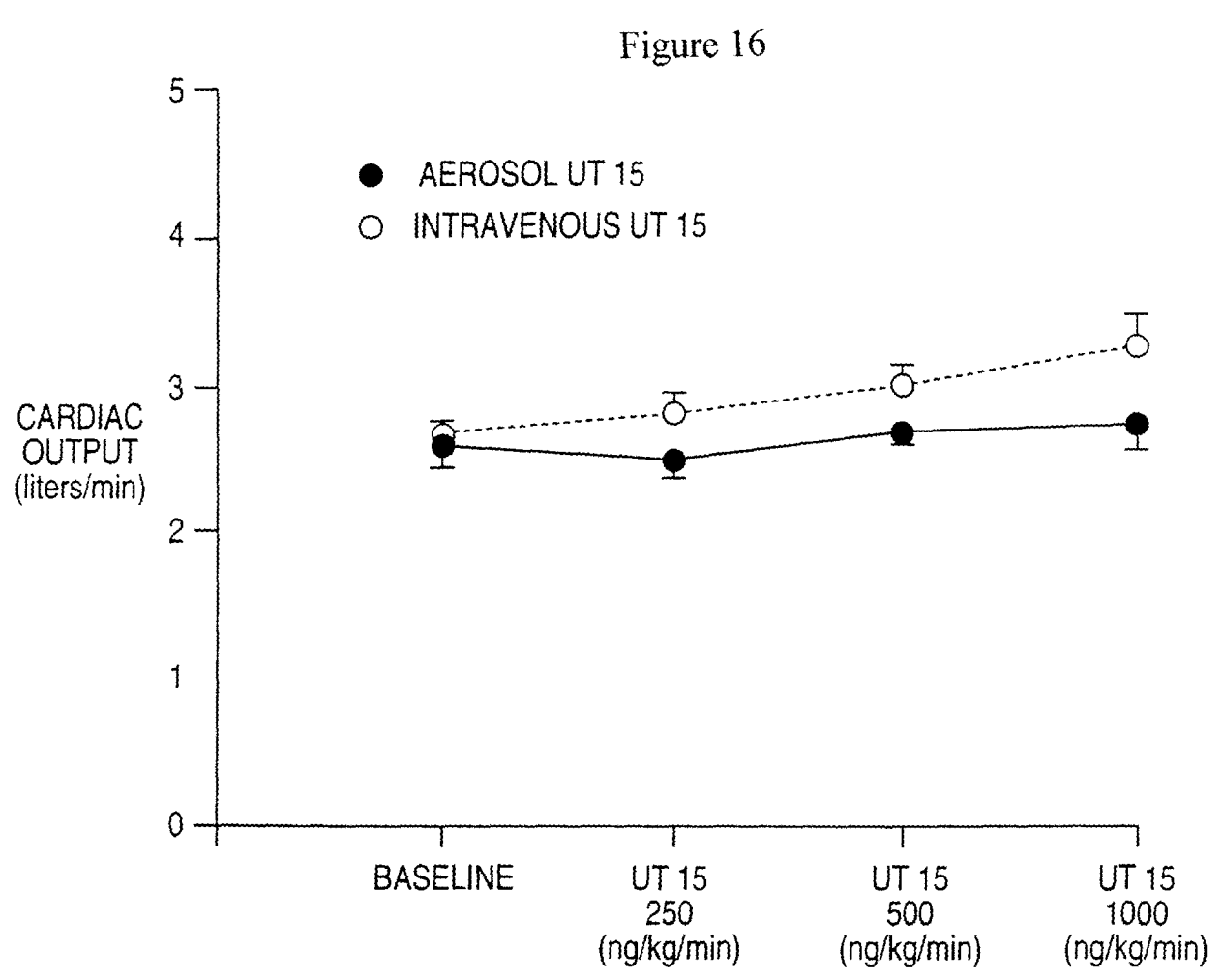

FIG. 16 depicts the effects on CO: no significant changes were observed for any delivery rate relative to the respective baseline values nor were any significant changes observed between the two modes of drug delivery.

Figure 17:
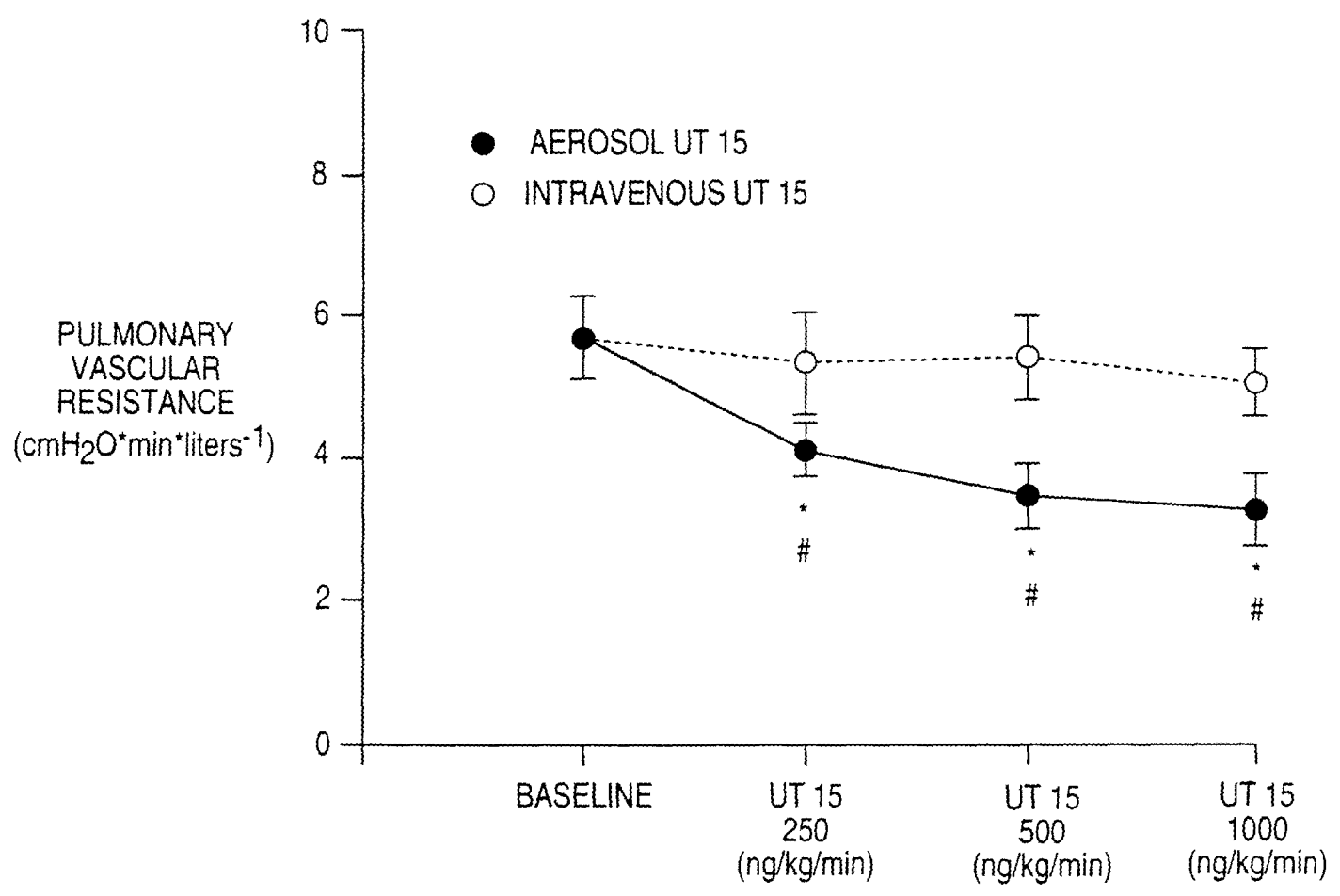

FIG. 17 represents the overall effect of aerosolized and intravenously infused UT-15 on the pulmonary circulation, PVR. Intravenous UT-15 had no significant effect on PVR whereas aerosolized UT-15 did cause a significant decrease at all 3 delivery rates.

Figure 25:
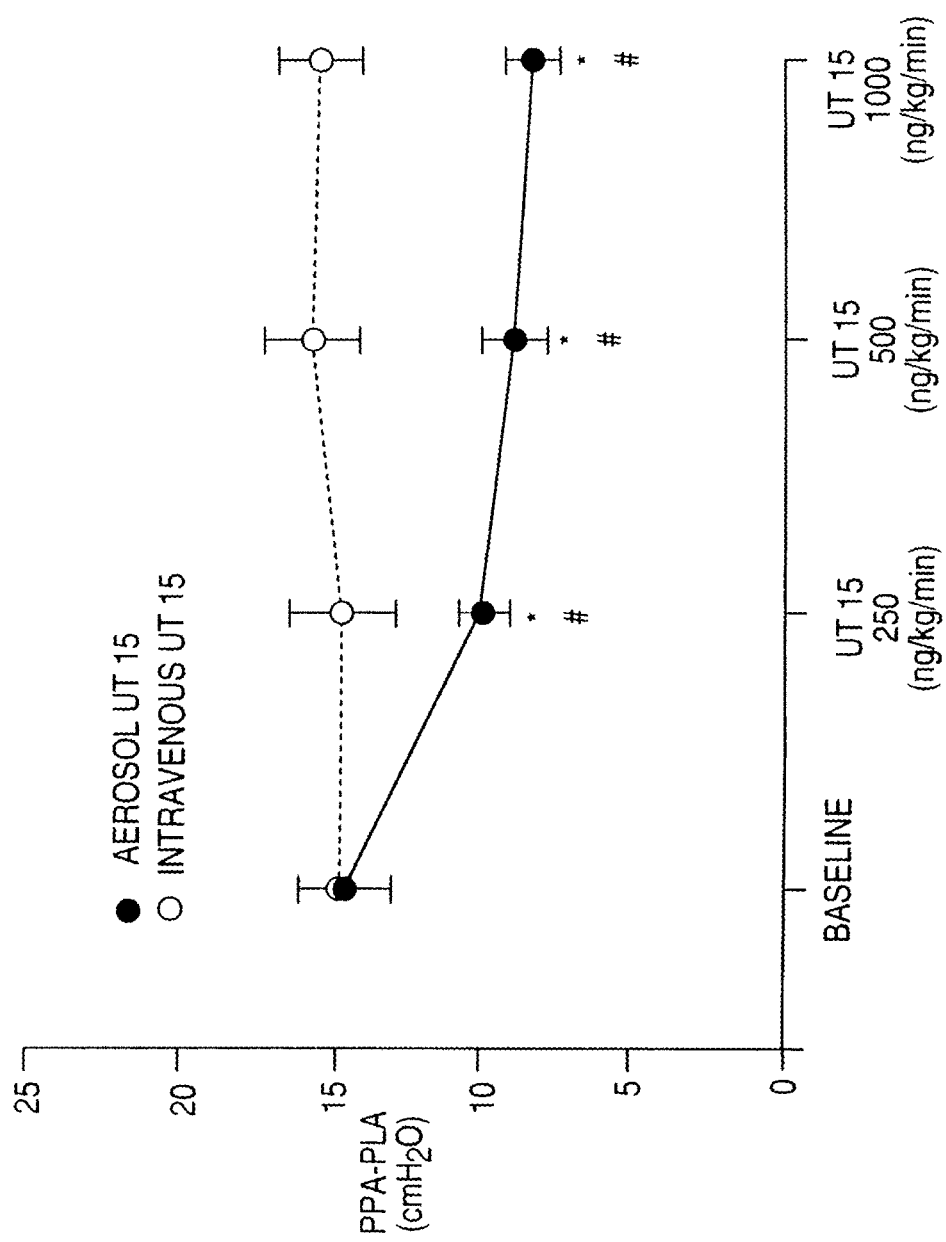

The decrease in PVR for aerosolized UT-15 at 250, 500, and 100 ng per kg per min is attributable to the small increase in PLA and small decrease in PPA. While neither of these variables were significantly different from the baseline values, the combinations (i.e., PPA minus PLA, used in Equation 2) were significant, as depicted in FIG. 25. Intravascularly infused UT-15 had no effect on PVR yet did have significant effects on heart rates. The statistical analysis of these data were done using rigorous two-way ANOVA and Student-Newman-Keuls tests, thus any statistical differences can be accepted with confidence.

Example V

Constricted Intravenous and Aerosolized UT-15 Dose Response

Two separate experiments were conducted to determine the dose response effects of intravenously infused UT-15 and aerosolized UT-15 during U44069 induced pulmonary hypertension. After a 30 minute baseline was established, U44069 was infused intravenously at a rate of 1 ng per kg per min. For the intravenous administration of UT-15 and after allowing the sheep to achieve a steady-state for 30-60 minutes, a dose-response to intravenous UT-15 was similar to that set forth in Example IV. For the aerosolized administration of UT-15 and after allowing the sheep to achieve a steady-state for 30-60 minutes, a dose-response to intravenous UT-15 was similar to that set forth in Example IV. In each experimental protocol, UT-15 was administered to three sheep for 30 minutes and to the other three sheep for 60 minutes.

No differences were found between 30 minute and 60 minute UT-15 delivery at each of the three rates of administration. The effects of U44069 and the subsequent dose-response effects of UT-15 during U44069 infusion on heart rate are shown in FIG. 10. Intravenous UT-15 caused heart rate to increase above the values during U44069 conditions, whereas aerosolized UT-15 had no effect on heart rate. In particular, for intravenous UT-15, the heart rate was significantly different relative to the baseline only at a delivery rate of 1000 ng per kg per min, whereas both 500 and 1000 ng per kg per min intravenous delivery of UT-15 were statistically different from the U44069 values. Both 500 and 1000 ng per kg per min aerosol delivery rates were different from their corresponding intravenous infusion delivery rates.

Figure 19:
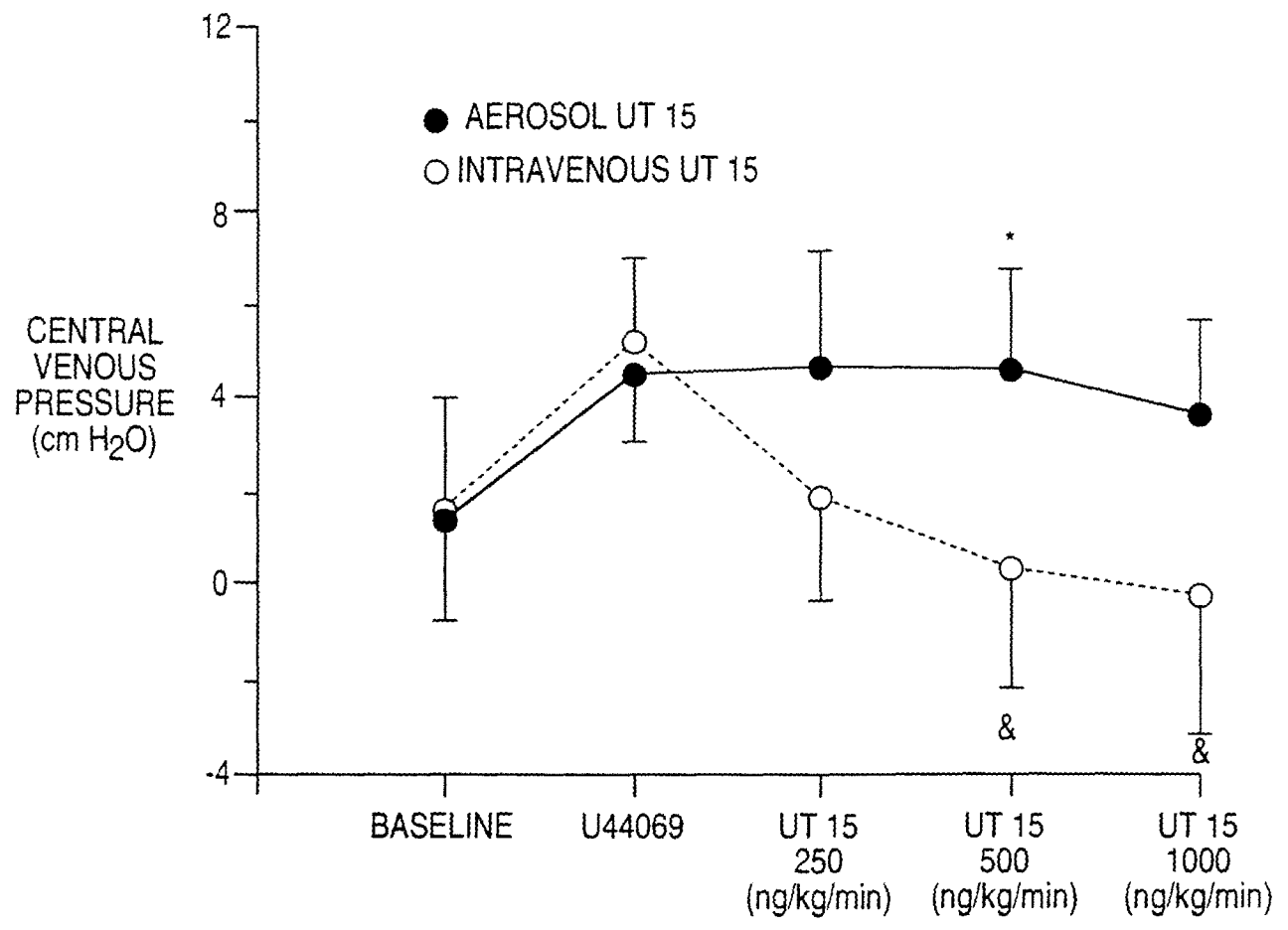

Data for central venous pressure are shown by FIG. 19. Some differences were noted for central venous pressure for intravenous UT-15, in that, at 500 and 1000 ng per kg per min delivery rates the values were different from the U44069 values. Only the 500 ng per kg per min aerosol value was different from the corresponding intravenous UT-15 infusion value.

Figure 20:
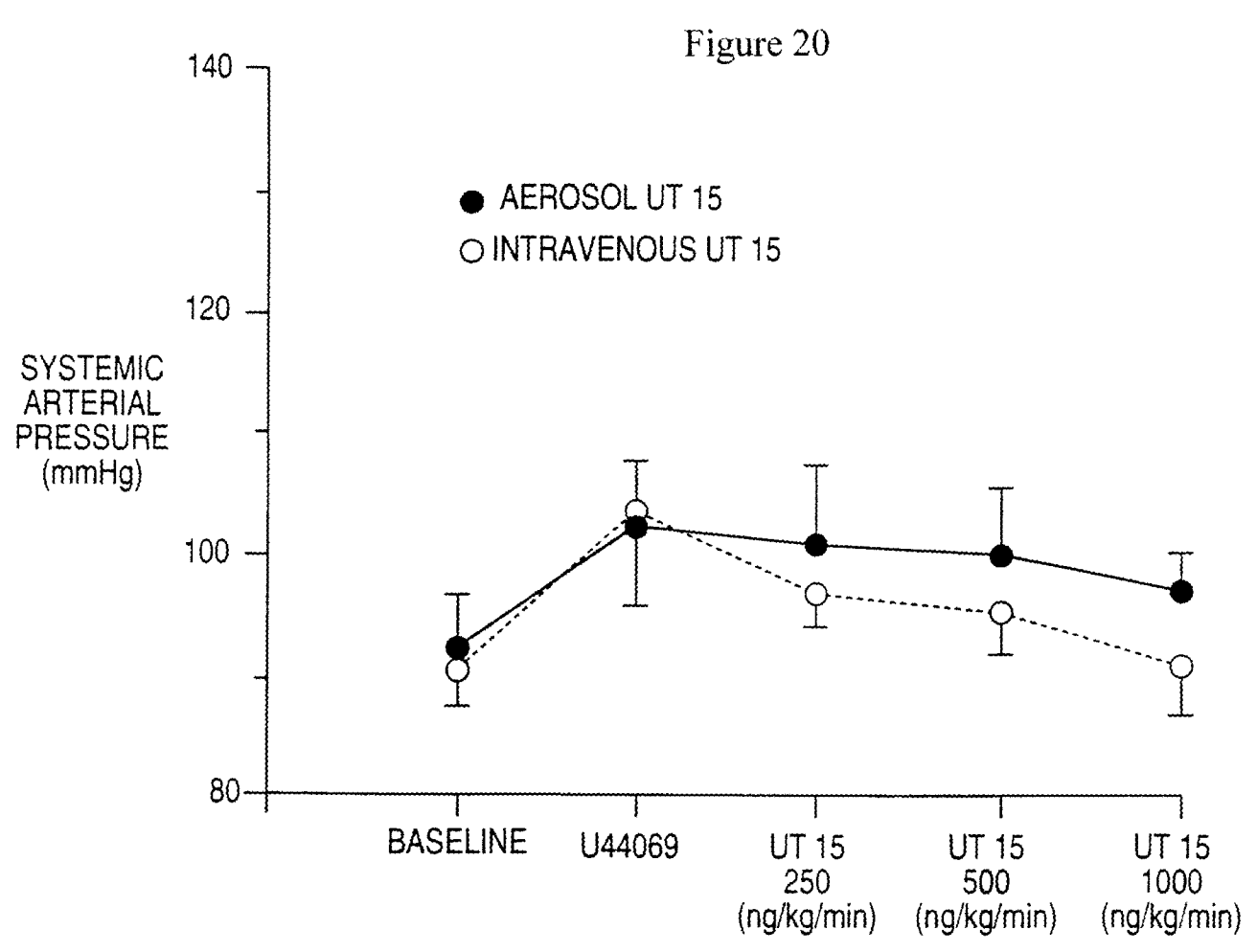
Figure 21:
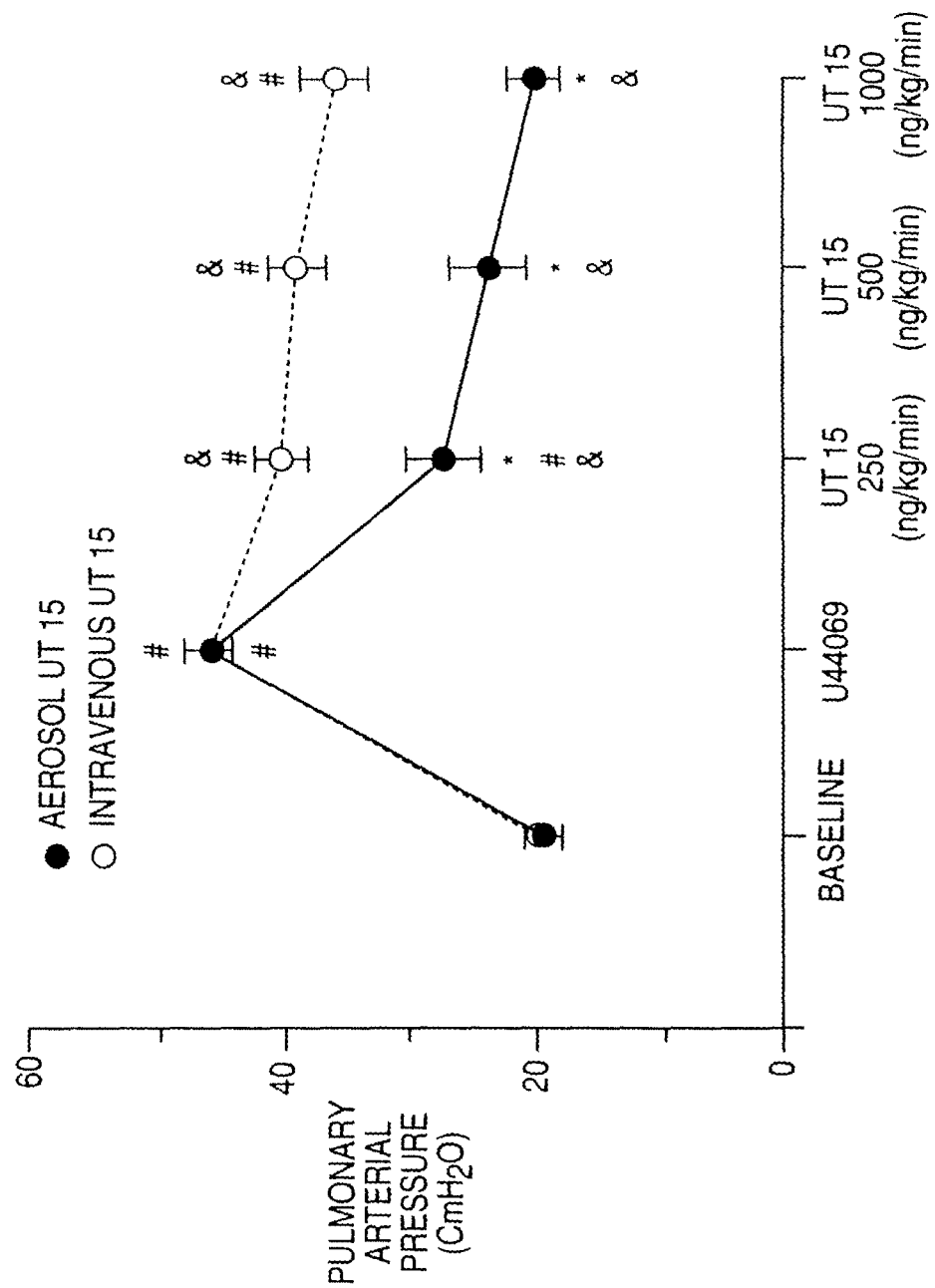

There were no statistical differences for the systemic arterial pressure for these series of experiments (FIG. 20). Pulmonary arterial pressure responses are illustrated by FIG. 21. U44069 significantly increased PPA relative baseline and all 3 delivery rates for significantly greater for aerosolized UT-15 for all 3 rates of drug delivery relative to intravenous delivery. In fact, for aerosolized UT 15 at 500 and 1000 ng per kg per min PPA was back to normal values.

Figure 22:
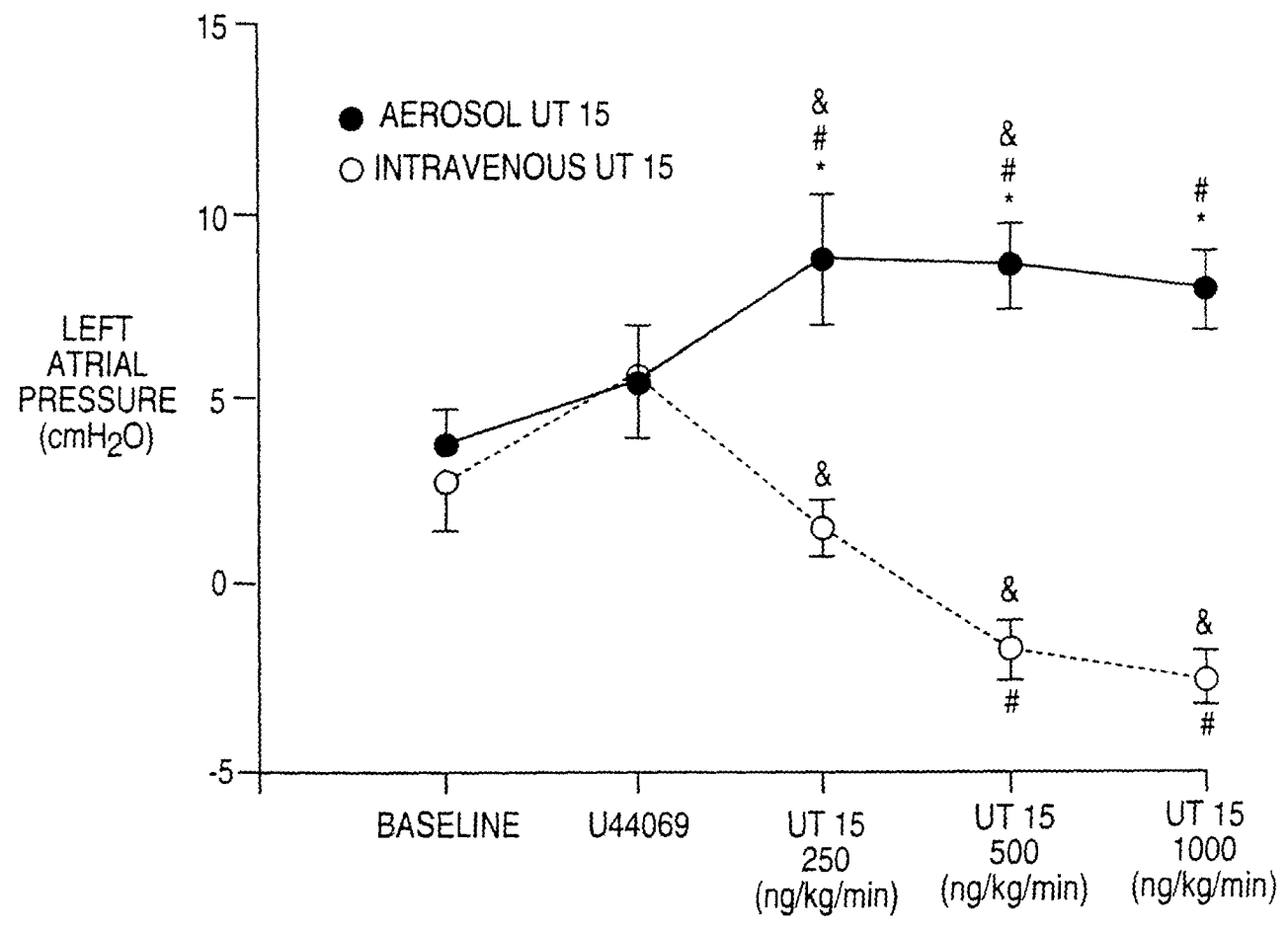

U44069 did not alter left atrial pressure significantly. However, intravenously infused UT-15 caused a significant decrease from the U44069 value at all three delivery rates and were different from the baseline values at 500 and 1000 ng per kg per min. All three aerosol delivery rates were increased above baseline, while 250 and 500 ng per kg per min were increased above the U44069 values. As can be seen from FIG. 22, all three aerosol delivery rate effects were different from the intravenously infused delivery rates.

Figure 23:
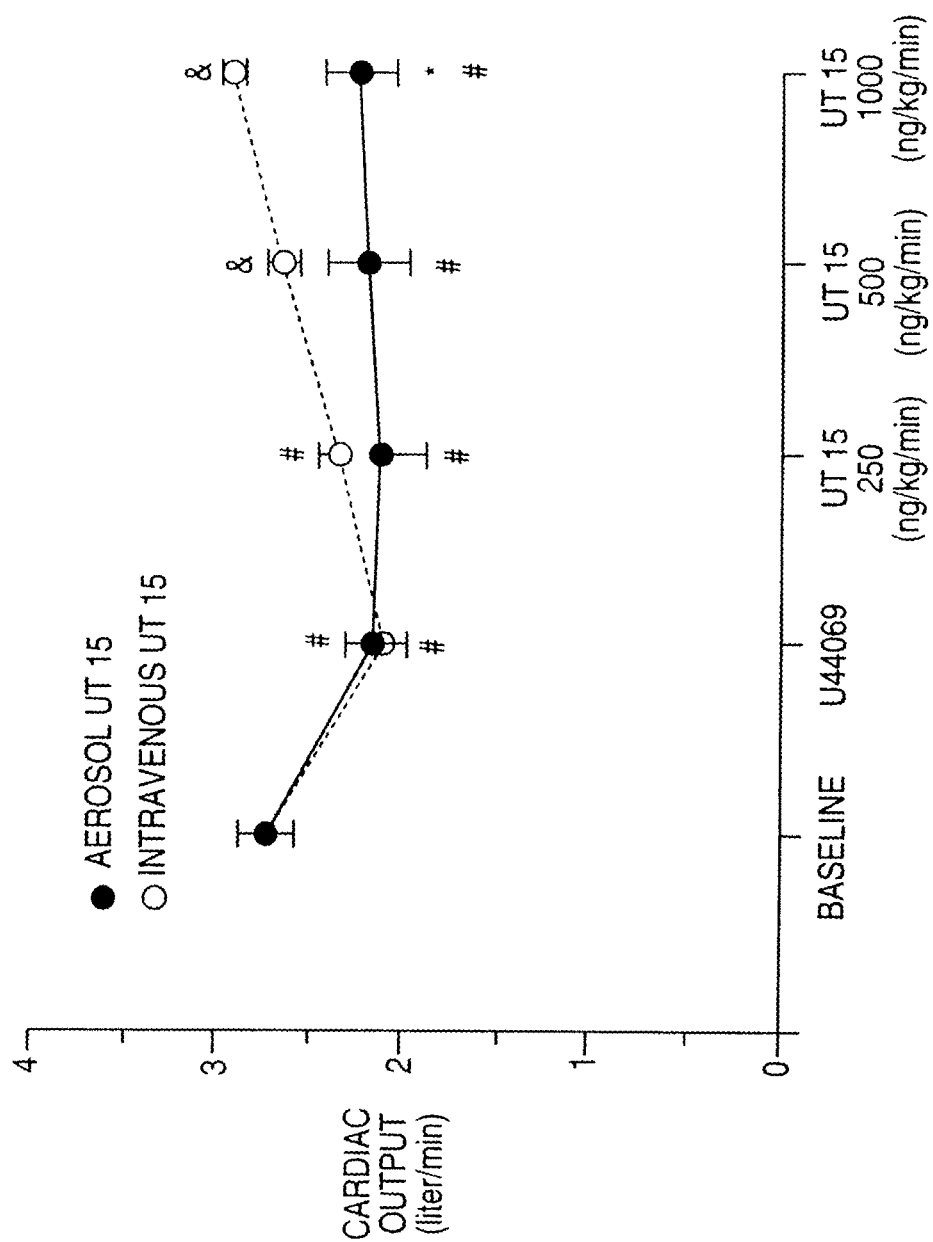

The most dramatic effects for UT-15 by either mode of administration were on cardiac output and the "lung variables." U44069 caused cardiac output to decrease from the baseline as depicted in FIG. 23. Aerosol UT-15 had no effect on cardiac output. Intravenous UT-15 caused a dose-response increase in cardiac output, which was significant at 500 and 100 ng per kg per min. At 1000 ng per kg per min, aerosolized UT-15 delivery was significantly different from the intravenously infused UT-15.

Figure 24:
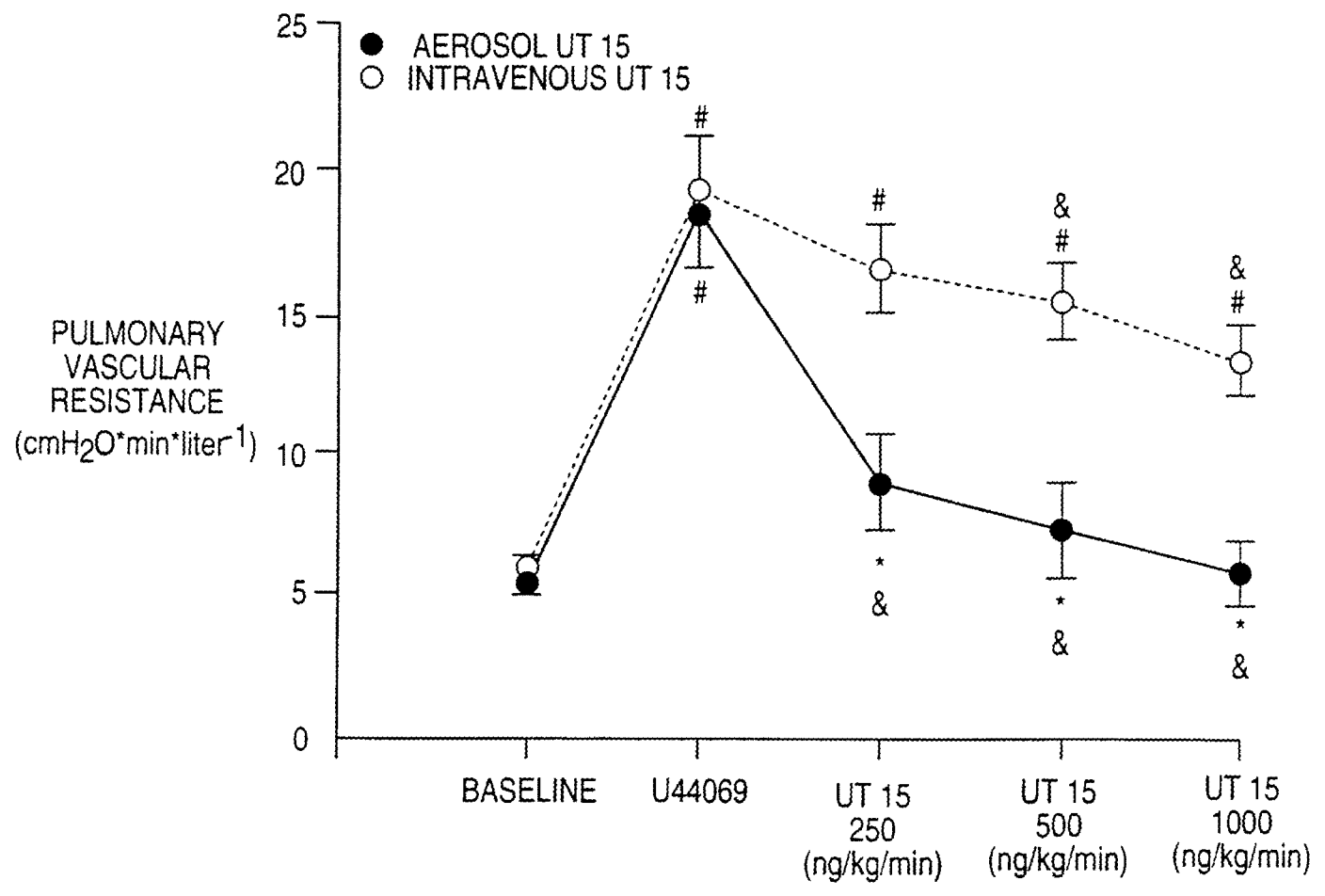

FIG. 24 graphically demonstrates the overall effects of intravenous and aerosol delivery of UT-15 on pulmonary vascular resistance during U44069. It shows that pulmonary vascular resistance, while being significantly attenuated by both intravascularly infused and aerosolized UT-15, was more affected by aerosolized UT-15. In particular, U44069 caused a dramatic increase in PVR, which was significantly attenuated at 500 and 1000 ng per kg per min for intravenously infused UT-15. Aerosolized UT-15 caused PVR to decrease such that there was no significant difference for any of the three delivery rates relative to the baseline PVR. Interestingly, the time at which intravenous and aerosol UT-15 began to attenuate the increase in PVR were very similarly (4-5 minutes), whereas the off response for aerosolized UT-15 was much longer than intravenous UT-15 (43 vs. 12 minutes).

Figure 26:
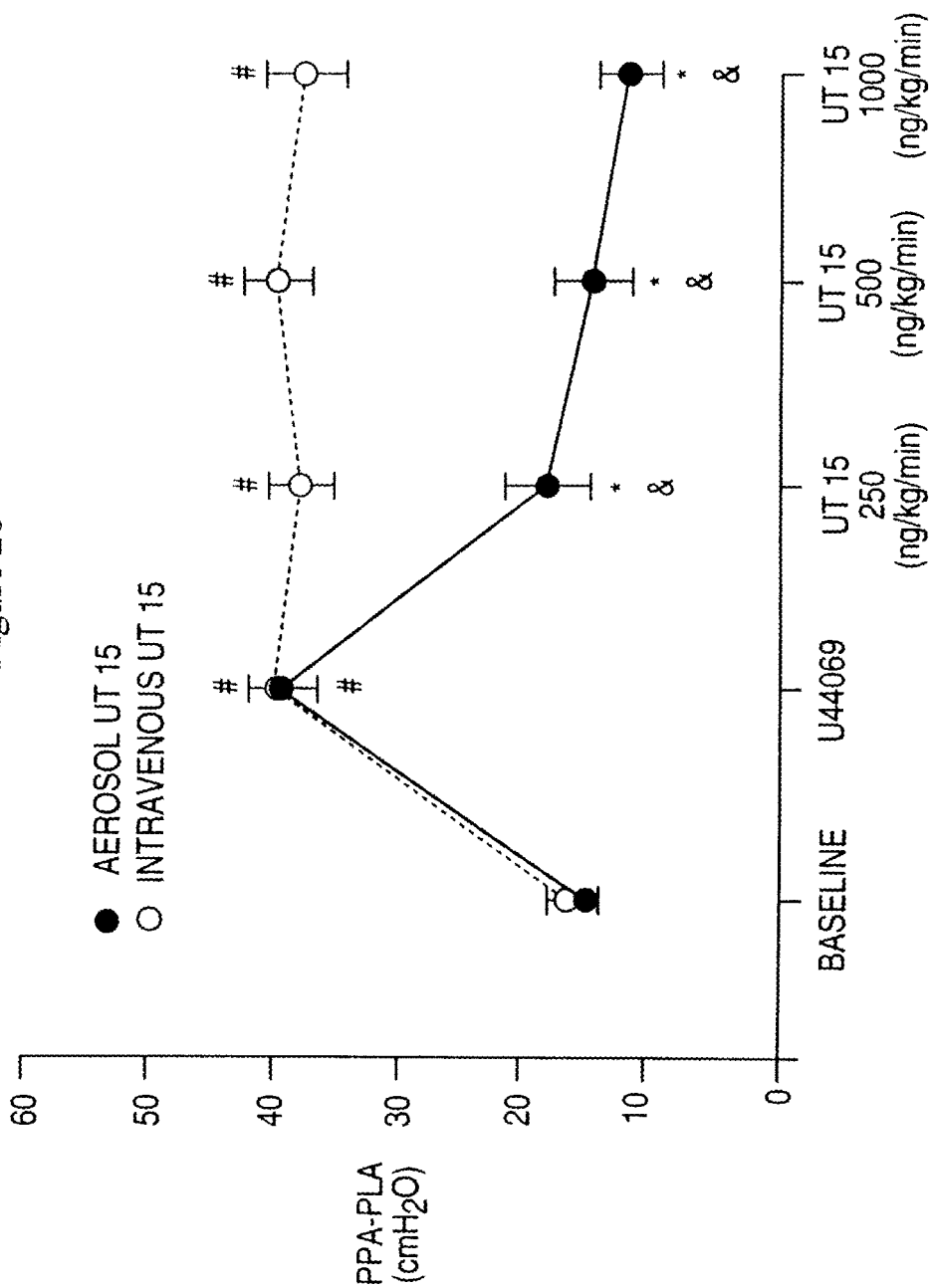

FIG. 26 shows that although intravascular UT-15 caused PPA to decrease significantly from the UT44069 value, this decrease matched by a decrease in PLA. Therefore, the pulmonary vascular driving pressure (PPA-PLA) was unchanged.

Additional Disclosure

In one embodiment, the disease or condition that causes ischemic lesions comprises scleroderma, Buerger's disease, Raynaud's disease and/or Raynaud's phenomenon. In another embodiment, the ischemic lesions comprise digital ischemic lesions, such as finger ulcers and/or necrotic lesions. In another embodiment, the disease or condition that that causes ischemic lesions comprises systemic schlerosis. In an additional embodiment, pain and/or other symptoms associated with digital ischemic lesions are reduced, eliminated or prevented upon administration of an effective amount of Treprostinil and/or its derivatives, and/or pharmaceutically acceptable salts thereof.

The present invention also relates to kits for accomplishing such treatment or prevention of ischemic lesions. The invention includes a kit for treatment and/or prevention of ischemic lesions in a subject with a disease or condition that causes ischemic lesions, comprising (i) an effective amount of Treprostinil or its derivatives, or pharmaceutically acceptable salts thereof, (ii) one or more pharmaceutically acceptable carriers and/or additives, and (iii) instructions for use in treating or preventing ischemic lesions. In one embodiment, the disease or condition that causes ischemic lesions comprises scleroderma, Buerger's disease, Raynaud's disease and/or Raynaud's phenomenon. In another embodiment, the ischemic lesions comprise digital ischemic lesions, such as finger ulcers and/or necrotic lesions. In another embodiment, the disease or condition that that causes ischemic lesions comprises systemic schlerosis.

Unless otherwise specified, the term "a" or "an" used herein shall mean "one or more."

As used herein, the phrase "instructions for use" shall mean any FDA-mandated labeling, instructions, or package inserts that relate to the administration of Treprostinil or its derivatives, or pharmaceutically acceptable salts thereof, for the purpose of treating or preventing ischemic lesions. For example, instructions for use may include, but are not limited to, indications for ischemic lesions, identification of specific symptoms associated with ischemic lesions, such as digital ulcers or pain, that can be ameliorated by Treprostinil, and recommended dosage amounts for subjects suffering from ischemic lesions.

The term "acid derivative" is used herein to describe C1-4 alkyl esters and amides, including amides wherein the nitrogen is optionally substituted by one or two C1-4 alkyl groups.

The invention also includes bioprecursors or "pro-drugs" of Treprostinil, that is, compounds which are converted in vivo to Treprostinil or its pharmaceutically active derivatives thereof.

Further aspects of the present invention are concerned with the use of Treprostinil or its derivatives, or pharmaceutically acceptable salts thereof, in the manufacture of a medicament for the treatment or prevention of ischemic lesions in subjects with Buerger's disease, scleroderma, Raynaud's disease, Raynaud's phenomenon, or other conditions.

The present invention also encompasses methods of using Treprostinil or its derivatives, or pharmaceutically acceptable salts thereof. In one embodiment, a method uses Treprostinil sodium, currently marketed under the trade name of REMODULIN®. The FDA has approved Treprostinil sodium for the treatment pulmonary arterial hypertension by injection of dose concentrations of 1.0 mg/mL, 2.5 mg/mL, 5.0 mg/mL and 10.0 mg/mL. The chemical structure formula for Treprostinil sodium is:

Treprostinil sodium is sometimes designated by the chemical names: (a) [(1R,2R,3aS,9aS)-2,3,3a,4,9,9α-hexahydro-2-hydroxy-1-[(3S)-3-hydroxyoctyl]-1H-benz[ninden-5-yl]oxy]acetic acid; or (b) 9-deoxy-2',9-α-methano-3-oxa-4,5,6-trinor-3,7-(1',3'-interphenylene)-13,14-dihydro-prostaglandin $F_1$. Treprostinil sodium is also known as: UT-15; LRX-15; 15AU81; UNIPROST™; BW A15AU; and U-62,840. The molecular weight of Treprostinil sodium is 390.52, and its empirical formula is $C_{23}H_{34}O_5$.

The present invention extends to methods of using physiologically acceptable salts of Treprostinil, as well as non-physiologically acceptable salts of Treprostinil that may be used in the preparation of the pharmacologically active compounds of the invention.

Physiologically acceptable salts of Treprostinil include salts derived from bases. Base salts include ammonium salts (such as quaternary ammonium salts), alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

The amount of Treprostinil or its derivative, or a pharmaceutically acceptable salt thereof, that is required in a medication or diagnostic aid according to the invention to achieve the desired effect will depend on a number of factors, such as the specific application, the nature of the particular compound used, the mode of administration, the concentration of the compound used, and the weight and condition of the patient. A daily dose per patient for treatment or prevention of ischemic lesions may be in the range 25 µg to 250 mg; 0.5 µg to 2.5 mg, or 7 µg to 285 per day per kilogram bodyweight. For example, an intravenous dose in the range 0.5 µg to 1.5 mg per kilogram bodyweight per day may conveniently be administered as an infusion of from 0.5 ng to 1.0 µg per kilogram bodyweight per minute. One possible dosage is 2.5 ng/kg/min, increased over 12 weeks by an amount of 2.50 ng/kg/min each week, until a target dose, such as 15 ng/kg/min, is reached. Infusion fluids suitable for this purpose contain, for example, from 10 ng to 1 µg per milliliter. Ampoules for injection contain, for example, from 0.1 µg to 1.0 mg and orally administrable unit dose formulations, such as tablets or capsules, contain, for example, from 0.1 to 100 mg, typically from 1 to 50 mg. For diagnostic purposes, a single unit dose formulation may be administered. In the case of physiologically acceptable salts, the weights indicated above refer to the weight of the active compound ion, that is, the ion derived from Treprostinil.

In the manufacture of a medicament or diagnostic aid according to the invention, hereinafter referred to as a "formulation," Treprostinil and/or its derivatives, and/or pharmaceutically acceptable salts thereof, may be admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.05% to 95% by weight of the active compound. One or more of Treprostinil or its derivatives, or pharmaceutically acceptable salts thereof, may be incorporated in the formulations of the invention, which may be prepared by any of the well known techniques of pharmacy for admixing the components.

In addition to Treprostinil, other pharmacologically active substances may be present in the formulations of the present invention which are known to be useful for treating ischemic lesions in subjects with scleroderma, Buerger's disease, Raynaud's disease, Raynaud's phenomenon, or other conditions. For example, the compounds of the invention may be present in combination with analgesics to treat pain, dressing changes, vasodilator medications, and topical or oral antibiotics.

The formulations of the invention include those suitable for parenteral (e.g., subcutaneous, intramuscular, intradermal, or intravenous), oral, inhalation (in solid and liquid forms), rectal, topical, buccal (e.g., sub-lingual) and transdermal administration, although the most suitable route in any given case may depend on the nature and severity of the condition being treated and on the nature of the particular form of Treprostinil, its derivative, or a pharmaceutically acceptable salt thereof, which is being used.

Formulations of the present invention suitable for parenteral administration conveniently comprise sterile aqueous preparations of Treprostinil or its derivative, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations according to the invention may contain from 0.1 to 5% w/v of active compound and may be administered at a rate of 0.1 ml/min/kg. Alternatively, the invention may administered at a rate of 0.625 to 50 ng/kg/min. Alternatively, the invention may be administered at a rate of 10 to 15 ng/kg/min.

Formulations suitable for oral administration may be presented in discrete units, such as capsules, cachets, lozenges, or tablets, each containing a predetermined amount of Treprostinil or its derivative, or a pharmaceutically acceptable salt thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising Treprostinil or its derivative, or a pharmaceutically acceptable salt thereof, in a flavored base, usually sucrose and acacia or tragacanth;

and pastilles comprising the compound in an inert base such as gelatin and glycerin or sucrose and acacia.

Formulations suitable for rectal administration are preferably presented as unit dose suppositories. These may be prepared by admixing Treprostinil or its derivative, or a pharmaceutically acceptable salt thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w. Formulations for transdermal administration may be delivered by iontophoresis (see, for example, *Pharmaceutical Research,* 3(6): 318 (1986)) and typically take the form of an optionally buffered aqueous solution of Treprostinil or its derivative or salt or thereof. Suitable formulations comprise citrate or bis/tris buffer (pH 6) or ethanol/water and contain from 0.1 to 0.2M active ingredient.

The compounds of the present invention are conveniently prepared by methods the same as or analogous to those described in U.S. Pat. Nos. 4,306,075, 6,528,688 and 6,441,245.

Additional embodiments are within the scope of the invention. For example, in one embodiment, a method for treating or preventing ischemic lesions in a subject, such as a human being, with a disease or condition that causes ischemic lesions comprises administering to a subject in need thereof an effective amount of Treprostinil or its derivative, or a pharmaceutically acceptable salt thereof.

In another embodiment, a kit for treatment or prevention of ischemic lesions in a subject with a disease or condition that causes ischemic lesions comprises (i) an effective amount of Treprostinil or its derivative, or a pharmaceutically acceptable salt thereof, (ii) one or more pharmaceutically acceptable carriers and/or additives, and (iii) instructions for use in treating or preventing ischemic lesions.

In certain embodiments, the disease or condition that causes ischemic lesions comprises scleroderma, Buerger's disease, Raynaud's disease and/or Raynaud's phenomenon. In one embodiment, the ischemic lesions comprise digital ischemic lesions. In another embodiment of the method, pain or other symptom associated with digital ischemic lesions is reduced, eliminated or prevented. The digital ischemic lesions include finger ulcers and/or necrotic lesions. In one embodiment, the disease or condition that that causes ischemic lesions comprises systemic schlerosis.

In certain method embodiments, the Treprostinil or its derivative, or a pharmaceutically acceptable salt thereof, is administered subcutaneously, by continuous subcutaneous infusion, intravenously, in an orally available form selected from the group consisting of tablets and capsules, and/or by inhalation. In other embodiments, the effective amount of Treprostinil or its derivative, or a pharmaceutically acceptable salt thereof, is at least 1.0 ng/kg of body weight/min.

In certain kit embodiments, the Treprostinil or its derivative, or a pharmaceutically acceptable salt thereof, is in a form suitable for subcutaneous administration, continuous subcutaneous infusion, intravenously administration or inhalation. In other kit embodiments, the Treprostinil or its derivative, or a pharmaceutically acceptable salt thereof, is in an orally available form selected from the group consisting of tablets and capsules. In another kit embodiment, the effective amount of Treprostinil or its derivative, or a pharmaceutically acceptable salt thereof, is at least 1.0 ng/kg of body weight/min.

In certain other method embodiments, the disease or condition that causes ischemic lesions comprises systemic sclerosis, and the ischemic lesions comprise digital ischemic lesions, and continuous administration of Treprostinil or its derivative, or a pharmaceutically acceptable salt thereof, promotes the healing of at least one digital ischemic lesion, and reduces or prevents the development of new digital ischemic lesions. In another embodiment, a method for reducing, eliminating or preventing pain and disability associated with ischemic lesions (such as digital ischemic lesions) in a subject with a disease or condition that causes ischemic lesions comprises administering to a subject in need thereof an effective amount of Treprostinil or its derivative, or a pharmaceutically acceptable salt thereof. In other embodiments, the subject is a human being, and the disease or condition that causes ischemic lesions comprises Buerger's disease that does not improve with smoking cessation. In another embodiment, the Treprostinil or its derivative, or a pharmaceutically acceptable salt thereof, is administered by continuous subcutaneous infusion by an infusion pump.

Additional Examples

Example VII

Administration of Treprostinil to Humans with Scleroderma Suffering from Digital Ischemic Lesions Scleroderma patients having at least one lesion (i.e., small sore or area of tissue gangrene) present on a hand or finger are dosed with increasing amounts of Treprostinil over 12 weeks. The medication is delivered by a small pump that is connected to a catheter placed under the skin. In this manner, increasing dosages of Treprostinil are administered to patients by chronic continuous subcutaneous infusion.

Specifically, a 1.0 mg/mL formulation of Treprostinil sodium) (REMODULIN® is administered subcutaneously using a standard micro-infusion, positive-pressure infusion pump designed for subcutaneous drug delivery (Mini-Med). Patients receive an initial dose of 2.5 ng/kg/min of study drug. If, in a given patient, a dose of 2.5 ng/kg/min is not tolerated (e.g., persistent headache, nausea, emesis, restlessness, anxiety or severe pain at infusion site that cannot be adequately managed by medication or topical treatment), the dose is reduced to 1.25 ng/kg/min. Patients are maintained at 2.5 ng/kg/min (or 1.25 ng/kg/min if 2.5 ng/kg/min is not tolerated) during Week 1. After that, the dose is raised by 2.50 ng/kg/min each week until not tolerated or once a target dose is reached.

Dosing is increased weekly unless not tolerated by the patient. Weekly dose increases do not exceed 2.50 ng/kg/min each. One example of a target dose is 15 ng/kg/min. The minimum dose is usually not less than 0.625 ng/kg/min. After completion of the Week 12 treatment, drug infusion are terminated by gradual reduction of the infusion rate (over a period of 1-4 hours, as clinically indicated) until a rate of 0 ng/kg/min is reached.

Patients receiving the above-described treatment experience fewer new lesions associated with scleroderma, and see a reduction in the number, size and severity of lesions present before treatment. The administration of Treprostinil treats and prevents digital ischemic lesions in patients with systemic sclerosis.

Example VIII

Study of Treprostinil (REMODULIN®) for the Treatment and Prevention of Digital Ischemic Lesions in Patients with Systemic Sclerosis Digital ischemic lesions (DIL) occur in up to 35% of patients with systemic sclerosis and are exquisitely painful, often progressing to necrosis requiring amputation. The purpose of this study was to evaluate the effect of Treprostinil on the healing and prevention of DIL in patients with systemic sclerosis.

Methods:

This study involved 12 subjects with diffuse or limited scleroderma with at least one DIL that had been present for 2 months or more (Table 1). Subjects who completed the study were treated for 12 weeks with Treprostinil and followed for another 8 weeks after drug discontinuation (FIG. 1).

Figure 4:
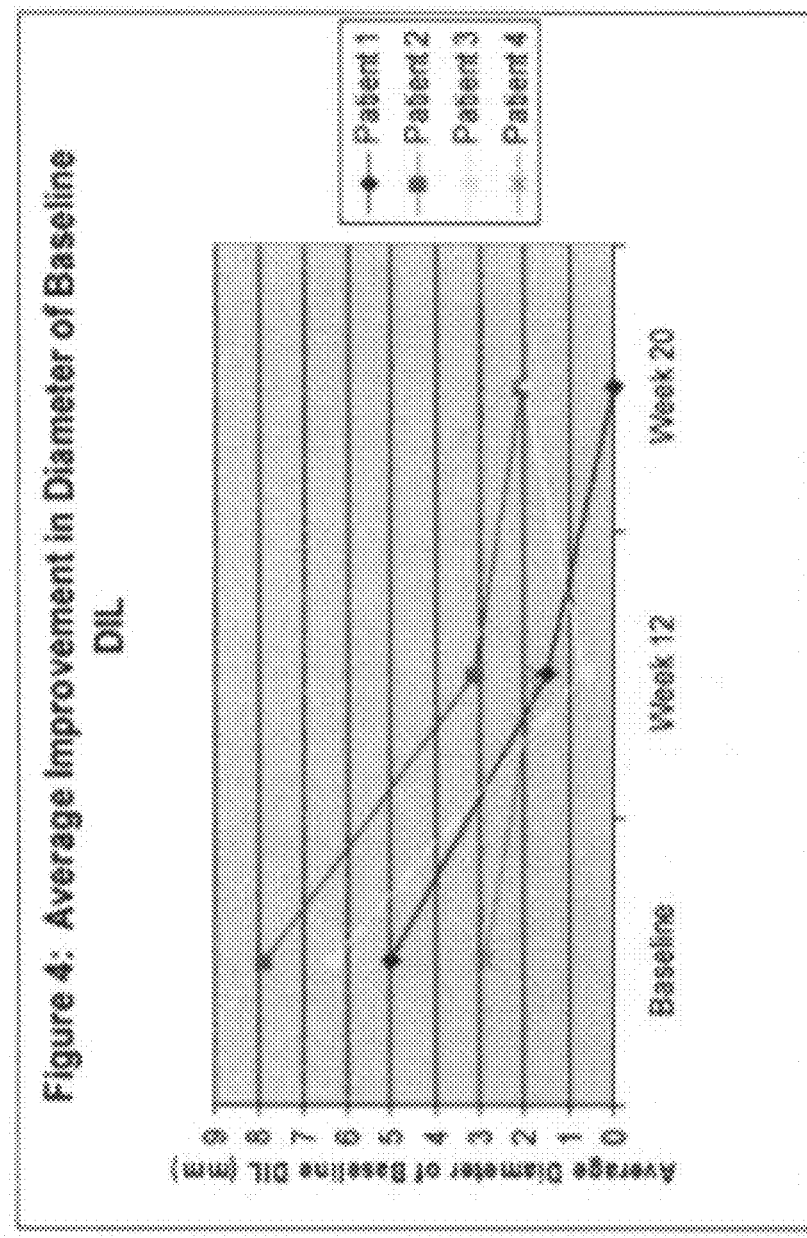
FIG. 4 is a graph showing the average improvement in diameter of baseline digital ischemic lesions.
Figure 5:
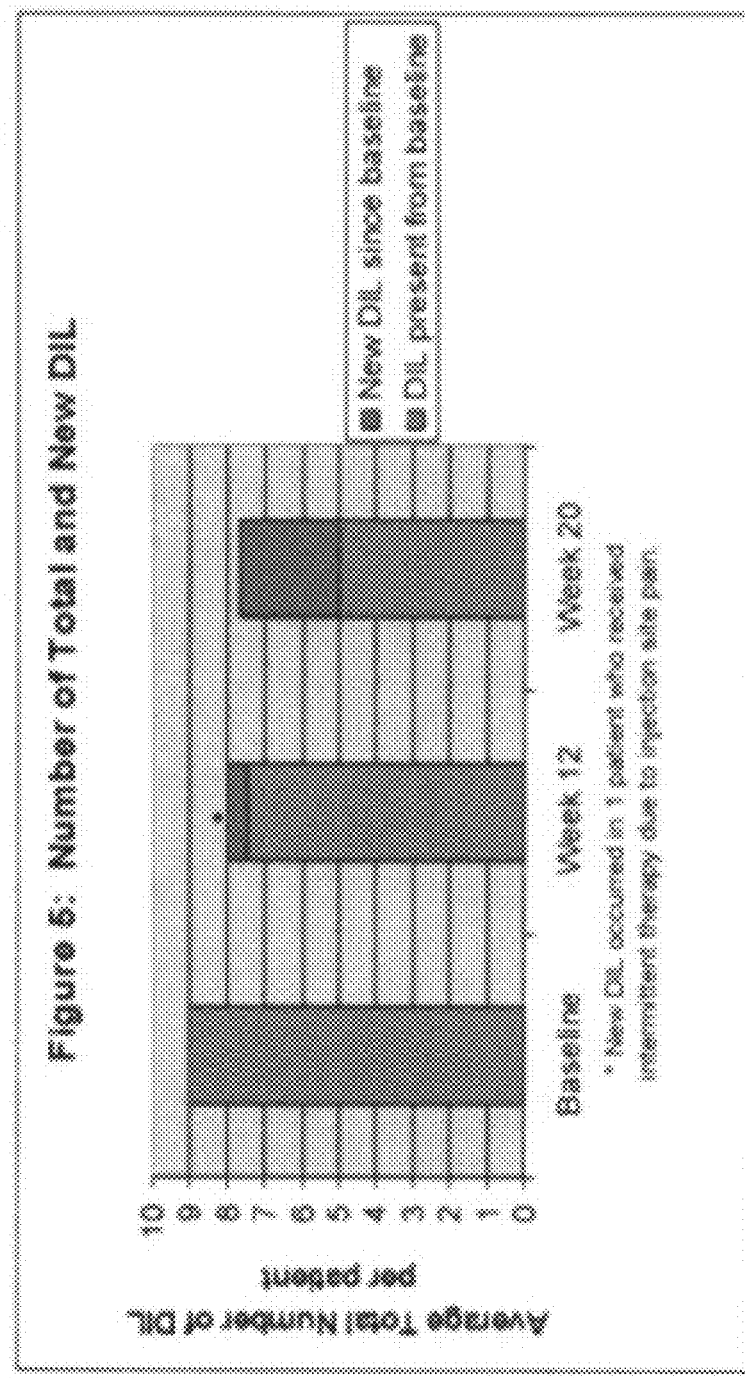
FIG. 5 is a bar graph showing the number of total and new digital ischemic lesions.
Figure 6:
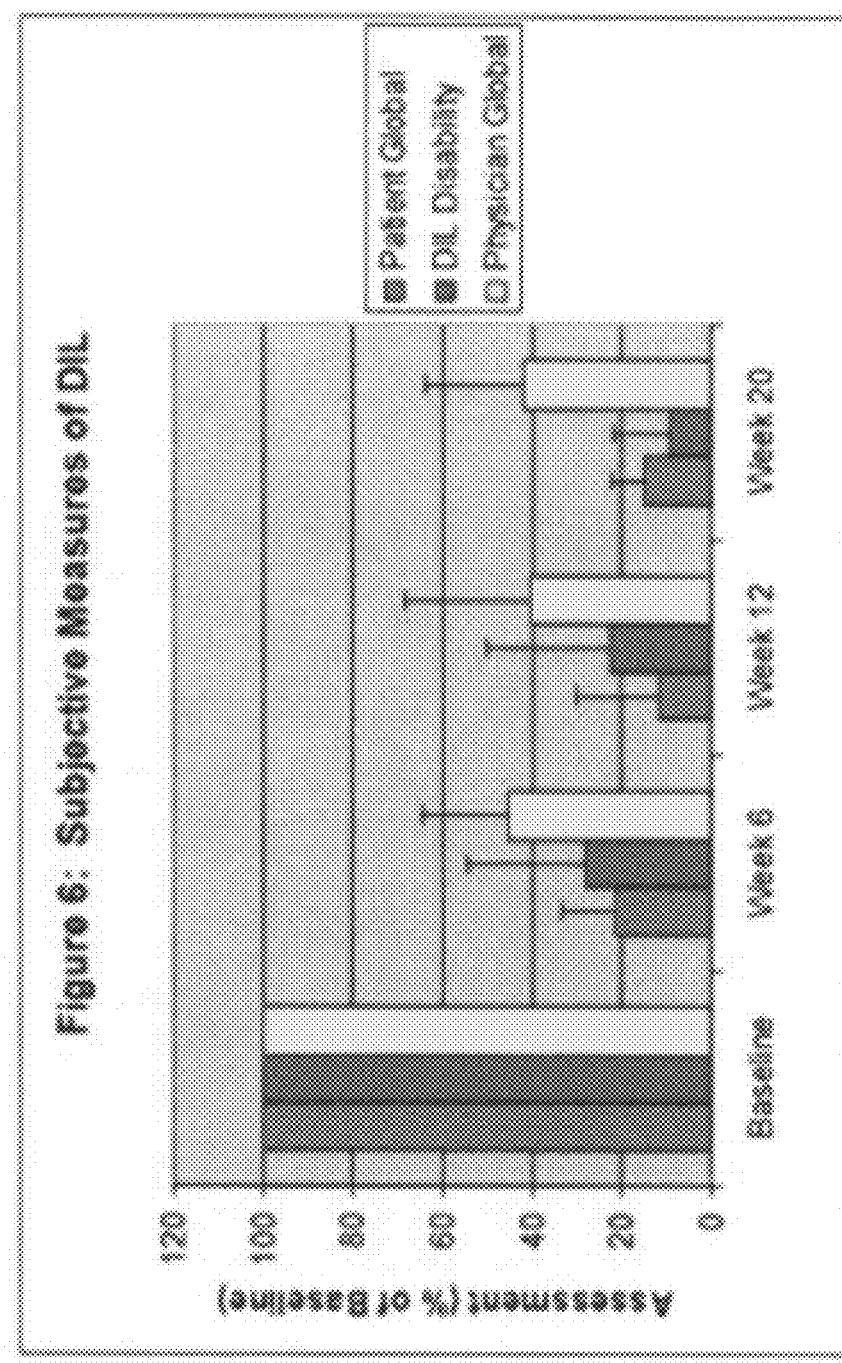
FIG. 6 is a bar graph showing the subjective measures of digital ischemic lesions
Figure 7:
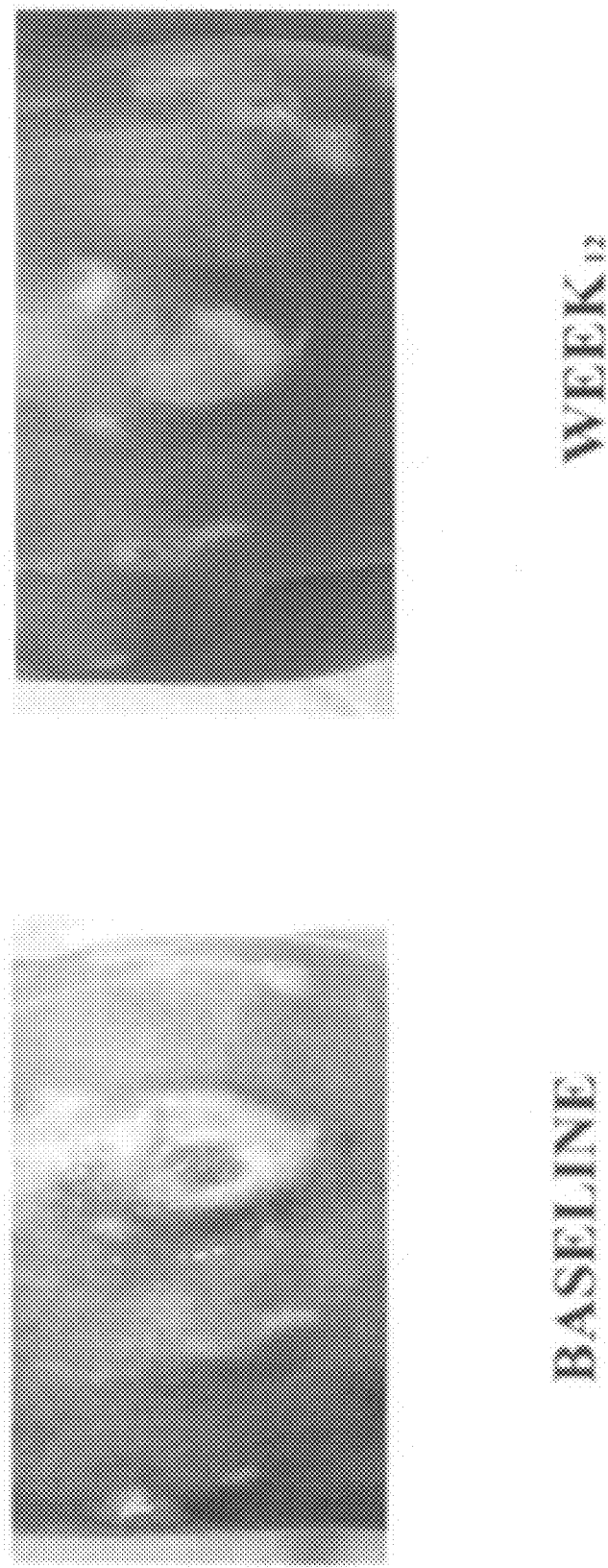
FIG. 7 shows the resolution of target digital ischemic lesions overlying 3rd metacarpophalangeal (MCP).

3). On average there was a 65% decrease in the size of baseline DIL (FIG. 4). No new ulcers developed in any patients while receiving continuous Treprostinil therapy (FIG. 5); however, two of three patients developed new ulcers during the 8-week follow-up period after drug discontinuation. By week 6, all five subjects demonstrated marked improvements in subjective measures of severity of their DIL according to patient and physician global assessment and DIL disability VAS scores. Physician global assessment of DIL severity improved on average by 60% after 12 weeks of therapy (FIGS. 6 and 7). Patient global assessment and DIL disability VAS scores improved on average by 89% and 77% respectively by week 12 (FIGS. 6 and 7).

Conclusion

This study indicates that continuous subcutaneous Treprostinil therapy is useful in the treatment and prevention of DIL in patients with systemic sclerosis. Continuous Treprostinil therapy promotes healing of DIL, and is useful in preventing the development of new DIL. The Treprostinil therapy also reduces pain and disability associated with DIL.

TABLE 1

| Baseline Patient Demographics | | | | | |
|---|---|---|---|---|---|
| Patient | 1 | 2 | 3 | 4 | 5 |
| Age (years) | 36 | 63 | 48 | 52 | 41 |
| Gender | Female | Female | Female | Female | Female |
| Limited v. Diffuse | Diffuse | Diffuse | Diffuse | Diffuse | Diffuse |
| Disease Duration (years) | 5.1 | 14.2 | 1.7 | 1.7 | 1.7 |
| Smoking History | Never | Never | Current | Remote[1] | Current |
| Antiphospholipid Antibodies | Yes | No | No | No | No |
| Other Risk Factors for Vasculopathy[2] | None | None | None | None | None |
| Concomitant Medications for Scleroderma (stable throughout study) | Nifedipine Losartan | Methotrexate Diltiazem Meloxicam Prednisone | Losartan Minocycline | Lisinopril Penicillamine Minocycline Celecoxib | None |
| Number of DIL | 5 | 25 | 3 | 7 | 9 |
| Size of Target Lesion (mm) | 7 | 10 | 10 | 5 | 5 |

[1]Remote history of smoking if quit greater than 10 years ago.
[2]Risk factors assessed for at screening included a history of sickle cell disease, lymphoma, leukemia, myeloma, paraproteinemia, cryoglobulinemia, cryofibrinogenemia, hepatitis C infection, or diabetes mellitus.

Treprostinil (REMODULIN®) was delivered to the subjects by continuous subcutaneous infusion, beginning at a rate of infusion of 2.5 ng/kg/min, which was increased by 2.5 ng/kg/min each week until a maximum rate of 15 ng/kg/min was achieved. Assessments were performed at baseline, weeks 2, 6, 12, 16, and 20. At each visit, the largest (target) lesion and other prominent DIL were measured by recording the largest diameter of the lesions. DIL were counted and photographed. Patient and physician global assessment of ulcers as well as patient assessment of disability from DIL were measured using visual analogue scales (VAS) at each visit.

Figure 2:
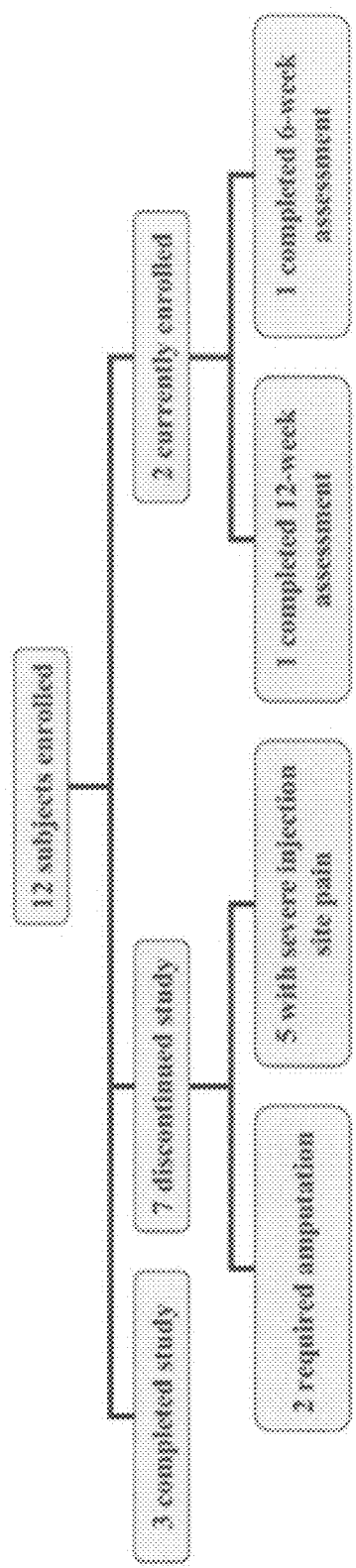
FIG. 2 indicates the disposition of the patients enrolled in the study.
Figure 3:
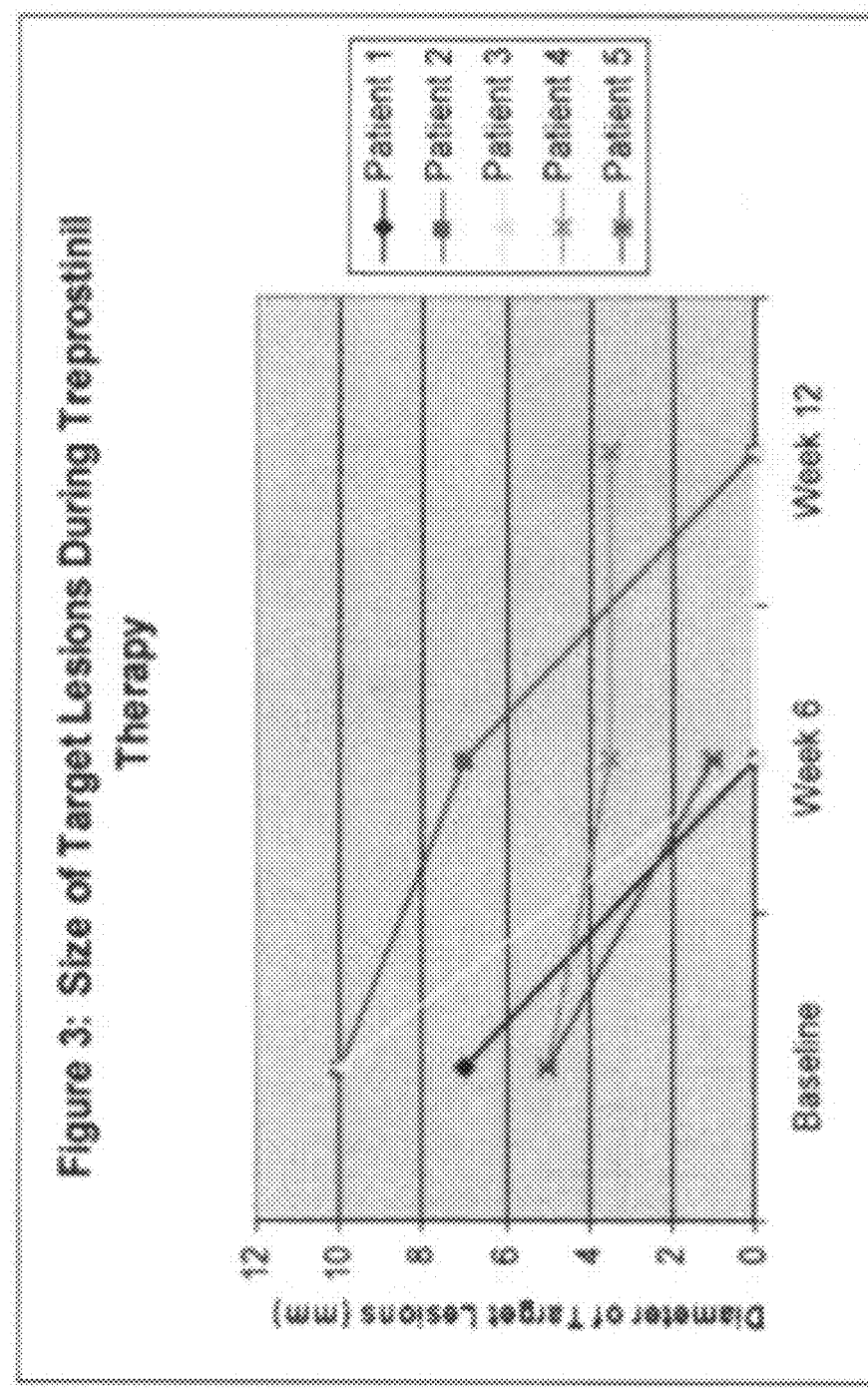
FIG. 3 is a graph showing the size of target lesions during Treprostinil therapy.

Results:

Three of the 12 subjects completed the study and two are currently still enrolled (FIG. 2). Two subjects discontinued the study for surgical treatment of previously ischemic digits, and five subjects were unable to complete the study due to intolerable injection site pain (FIG. 2).

Of the four subjects who completed 12 weeks of active therapy, target lesions improved in all patients, and three experienced complete resolution of their target lesions (FIG.

Example IX

Treprostinil Sodium Provides Symptom Relief in Severe Buerger's Disease

Background

Buerger's disease (thromboangiitis oliterans or TAO) is a clinical syndrome characterized by the development of segmental thrombotic occlusions of the medium and small arteries. The disease is clinically and pathologically distinguishable from atherosclerotic disease. Histopathology features may vary with the duration of the disease. In the chronic or end stage phase of the disease, only organized thrombus and fibrosis of the blood vessel is seen. In all stages of the disease, the normal structure of the vessel wall generally remains intact. Angiographic features of Buerger's disease are the involvement of small and medium sized vessels, segmental occlusive lesions, more severe disease distally and collateralization around areas of occlusion (corkscrew collaterals). Olin, Jeffery W., Current Concepts: Thromboangiitis Obliterans (Buerger's Disease), N. Engl. J. Med., Volume 343(12), 864-869 (Sep. 21, 2000).

It is typically seen in young men who are heavy smokers and is more common in Asian and eastern European countries than in the US. Smoking is generally considered a requirement for diagnosis. Proposed clinical diagnostic criteria are: 1) smoking history; 2) onset before the age of 50 years; 3) infra-popliteal arterial occlusions; 4) either upper limb involvement or phlebitis migrans; and 5) absence of atherosclerotic risk factors other than smoking. Shionoya, Shigehiko Diagnostic criteria of Buerger's Disease, International Journal of Cardiology 66 (Suppl. 1) S243-S245 (1998).

The primary treatment for Buerger's disease is cessation of cigarette smoking. Persistent or recurrent symptoms occur rarely in patients who quit smoking and maintain a tobacco free environment to exclude any second-hand smoke. In patients whose disease progresses despite smoking cessation, therapeutic options are limited. Revascularization is rarely indicated and usually not successful because of the diffuse and distal distribution of the disease. Mills, Jopseph L Sr. Buerger's Disease in the 21$^{st}$ Century: Diagnosis, Clinical Features, and Therapy, Seminars in Vascular Surgery, Vol. 16(3), 179-189 (September 2003).

Treprostinil sodium (REMODULIN®) is a stable analogue of prostacyclin with a plasma half life of more than 4 hours and is approved in the U.S. for chronic, continuous subcutaneous (SC) infusion in patients with pulmonary arterial hypertension (PAH). This case illustrates an example of a patients with severe and progressive Buerger's disease treated with a continuous subcutaneous infusion of treprostinil sodium in whom there were no other therapeutic options available.

Case Report

A 42 year old Cuban male was first seen in 2002 for evaluation of ischemic pain of his right hand. The patient had a complicated medical history of bilateral foot gangrene resulting in a left BKA (below the knee amputation) in 1991 and a right BKA in 1993. His only risk factor was a long history of heavy cigarette smoking. He began to experience right hand pain in 2002. An arteriogram revealed right hand ischemia with few distal targets amenable for revascularization. A trial of thrombolytic therapy was attempted, but abandoned 48 hours later and the patient was discharged on warfarin. Because of recurrent ischemic ulcers and arm claudication, the patient sought additional opinions by several other vascular specialists and was told nothing could be done.

The patient's condition was diagnosed in 2002 as Buerger's disease. This patient met all the Buerger's diagnostic criteria with the exception of a positive history of hyperlipidemia which had not been present at the time he first developed symptoms. Review of systems was negative for connective tissue disease. On physical examination, both brachial pulses were palpable but bilateral radial and ulnar pulses were absent. There was evidence of chronic ischemic changes in the right hand with loss of the digital fat pads. Allens test was abnormal bilaterally. There was a small area of necrosis beneath the nail of the right thumb. There was another ischemic necrotic ulcer in the distal phalanx of the right middle finger just proximal to the nail which measured 1 cm in length. Both hands turned completely white and the patient would complain of pain with elevation of the arms.

The patient had a long history of smoking but quit in 2002 when his claudication and ischemic symptoms recurred. He has no history of diabetes or hypertension. He is a recovering alcoholic but denies illicit drug use. There is no family history of thrombotic disorders, or hypercoagulable disorders. Laboratory findings were negative for connective tissue diseases. A hypercoagulable lab panel, including factor V Leiden, antithrombin III, protein C, protein S, prothrombin gene mutation, anticardiolipin antibody, and lupus anticoagulant, was unremarkable.

Cilostazol was added to pentoxifylline, simvastatin and narcotic analgesics but symptoms did not improve. In December 2002, his right index finger was amputated due to gangrene. At follow-up, there was still significant necrosis and ulceration of the right thumb. The patient was referred to Anesthesia and underwent several stellate ganglion blocks, again with no reported change in symptoms. Eventually, the right thumb required amputation. He was lost to follow-up (i.e., was under another care provider) for a short period of time and an ulcer that developed on the right index finger became infected and subsequently amputated.

Soon after, the patient exhibited disabling claudication symptoms primarily manifest as weakness in both arms, especially the left, and unable to carry out simply activities of daily living such as dressing himself or combing his hair. The right middle finger ulcer was not healing.

Noninvasive vascular testing revealed flat tracings in both upper extremities at the digital level with the left worse than the right. An arteriogram showed occluded right brachial artery at the elbow with severe distal disease and an occluded left brachial artery at the takeoff from the axillary artery with severe disease of the left hand. The arteriogram demonstrated "corkscrew collaterals" at several levels. It was felt that the patient might benefit from revascularization and a left axillary brachial artery bypass using human umbilical vein was performed. Despite therapeutic anticoagulation, the bypass went on to occlude.

At this point, subcutaneous Treprostinil therapy was administered to the patient. Treprostinil was delivered chronically by continuous subcutaneous infusion using a pager-sized ambulatory infusion pump (Medtronic Minimed 407C, Minneapolis, Minn.)). In September 2003, Treprostinil was started at 2.5 ng/kg/min and titrated by 1 ng/kg/min every 7 days until the patient reached his maximum tolerated dose of 12.5 ng/kg/min and was continued for the next 10 months. He was unable to tolerate higher doses due to diarrhea and jaw pain, commonly reported dose limiting side effects of prostacyclin therapy. The patient has reported improved comfort and increased ability to participate in activities of daily living such as dressing self, combing his hair, reaching above his head and driving. Doppler studies demonstrated improvement in pulse volume recording wave form. Attempts to discontinue Treprostinil resulted in return of ischemic symptoms within 1 week. The patient is now on a maintenance dose of Treprostinil 12 ng/kg/min from 9 PM-9 AM every seventh day, with no drug for the next 7 days. The patient has had sustained relief of symptoms on this regimen including complete healing of the ulcer on his right middle finger.

The patient's symptomatic improvements appear to be related to Treprostinil infusion. The patient's disease continued to progress despite quitting smoking in early 2002. We confirmed the patient was smoke free with a negative cotinine urine test in 2003 at the time he was started on Treprostinil. There has been continued improvement in pain and digital ulcer healing and an overall improvement in his quality of life. While there are no formal dosing recommendations from the manufacturer, our dosing regimen including the maintenance dosing appears safe and effective based on clinical improvement.

These results suggest that subcutaneous Treprostinil therapy is clinically useful in Buerger's disease that does not improve with smoking cessation, particularly in the presence of critical limb ischemia where other therapeutic options have failed. The ease of the application, similar to insulin pumps, make it an attractive therapeutic option versus more invasive intravenous delivery and is well tolerated Example X Treatment of Critical Limb Ischemia with Treprostinil Sodium (REMODULIN®) Reduces Rest Pain and Heals Ischemic Ulcers Background:

Treatment options are limited for patients with chronic critical limb ischemia (CLI), a life- and limb-threatening condition and the most severe form of peripheral arterial disease (PAD). Advanced CLI may lead to non-healing ischemic ulcer(s) and/or gangrene (*Thrombosis Research* 106(6): 295-301 (2002)).

The objectives of this study were an open-label, single-center evaluation of the safety and efficacy of continuous subcutaneous administration of treprostinil therapy in patients with CLI with no planned vascular interventional procedures and a determination of a safe dose of chronic treprostinil in these patients.

Methods:

The planned enrollment was ten patients. All patients were to have Fontaine Stage III-IV or Rutherford Class 4-6 disease and ankle brachial indexes (ABI) from 0-0.55 in the most affected limb or the limb containing the reference ischemic wound for wound healing assessments. Patients were excluded from the study if they had a vascular surgery or vascular procedure within 30 days of study entry, were hemodynamically unstable, had acute renal failure, acute pulmonary failure, history of recent intracranial bleed, gastric bleeding urinary tract bleeding or significant trauma within 6 weeks, a life-threatening malignancy requiring aggressive chemotherapy, end-stage renal disease and chronic renal dialysis. Any condition or abnormal laboratory value which, based on information in the treprostinil package insert, would constitute an unacceptable risk to the patient's safety, also was an exclusion criterion. Patients could not have been in an investigational trial within the past 30 days or been a non-responder to chronic prostanoid treatment in the past 30 days.

Medications for co-morbid disorders such as coronary artery disease or COPD, normal wound care, including debridement and antibiotics, and analgesics for rest pain were permitted during the study but were not to be changed from the baseline regimens unless clinically necessary.

After the completion of baseline assessments, treprostinil therapy was initiated in the clinic. Patients were observed for at least two hours following the initiation of treprostinil therapy. Patients and/or a caregiver were trained to administer treprostinil on an outpatient basis using an ambulatory subcutaneous infusion pump (Minimed, Sylmar, Calif., Model 407C). Each patient was to be initiated at a dose of 2.5 ng/kg/min or lower, with the dose titrated based on tolerability. Dose increases were to be 1.25-2.5 ng/kg/min per week. The maximum allowed dose was 15 ng/kg/min and the minimum allowed dose was 0.625 ng/kg/min. The patients were instructed to change the subcutaneous infusion site every three days.

Patients returned to the clinic for assessments at Weeks 2, 6, and 12. Treprostinil treatment was terminated by gradually decreasing the infusion rate (over a period of 1-4 hours, as clinically indicated) after the Week 12 visit assessments were completed.

Safety was assessed in all patients using adverse event (AEs) and physical examination findings. Signs and symptoms of CLI or worsening CLI were not considered to be AEs unless found to be different in causality, intensity, or frequency.

Rest pain was assessed in all patients using a visual analog scale (VAS) for rest pain. The patients were asked to rate their leg pain on a scale of 0-10 with 0 reflecting no pain and 10 reflecting the worst pain. The scale was printed and the patients were asked to place a mark on the number that reflected their pain experience. Patients were asked to rate the worst pain they had experienced since the previous assessment and their average pain during that time frame. Analgesic medication use was assessed by the investigator as unchanged, increased, decreased, or discontinued.

Wound assessments were to be conducted in patients who had at least one ischemic wound at baseline. If the patient had multiple ischemic wounds, then one or two (usually the largest or most severe wounds) were be selected as reference wounds. The selected wound(s) was photographed for documentation. When possible, the outside edge of the wound(s) was traced for area measurement. The tracings were used to calculate wound area by measuring the length and width of the wound. Not all wounds were of the nature that tracings were possible for example, wounds between toes or on the heel with extensive tissue loss were not traced. These wounds were described and photographed. The wound(s) was assessed for overall status compared to baseline (i.e., worse, slightly worse, unchanged, slightly improved, improved or healed) at study visits.

In patients who had wounds other than those chosen as reference wounds, the overall status (i.e., worse, the same, improved, or healed) of each additional wound also was documented at each study visit. Any new wounds that occurred during the study also were carefully documented.

TABLE 2

| Patient Characteristics (n = 10) | | |
|---|---|---|
| Age | Range 65-90 | 82.4 (mean) |
| Sex | 4 males | 40% |
| CAD/CHF | 9 | 90% |
| Hypertension | 5 | 50% |
| TIA/Stroke | 3 | 30% |
| COPD | 2 | 20% |
| DM | 4 | 40% |
| Renal Insufficiency | 4 | 40% |
| GERD | 3 | 30% |
| Lesion sites | | |
| SFA | 10 | 100% |
| Infra-popliteal | 7 | 70% |

Results:

Safety: Ten patients (six females) were enrolled in the study after written consent. The mean age was 82.4 years and ranged from 65-90. Eight patients had established coronary artery disease, four were diabetic, and three had chronic renal insufficiency. All patients had diffuse PAD involving the superficial femoral artery (SFA). Infra-popliteal disease was present in 7 patients. Six patients had bilateral limb involvement. One patient had a previous below the knee amputation (BKA) due to PAD. Three patients had failed by-pass grafts and one had a failed angioplasty. All patients met criteria for Fontaine Stage IV (Rutherford 5 or 6) disease with ischemic rest pain and at least one ischemic limb wound. Table 3 summarizes the patient demographics and disease status.

All patients received subcutaneous treprostinil. All patients received an initial dose of 2.5 ng/kg/min of study drug. Nine patients were titrated to the maximum dose of 15 ng/kg/min between week 1-6. One patient elected to stay at 7.5 ng/kg/min due to severe site infusion pain.

The most common sided effect reported was infusion site pain. Two patients experienced mild jaw pain, one patient reported a mild headache and one patient experienced diarrhea. These side effects were resolved generally by decreasing the treprostinil dose. Two patients discontinued drug prematurely. One patient discontinued at week eight related to severe site pain, jaw pain, headache and diarrhea. One patient felt overwhelmed by the pump and infusion site changes and withdrew consent at week six but reported only mild infusion site pain.

There were two serious adverse event (SAEs). One female patient had a cholecystectomy at week 10 with normal post operative recovery. Treprostinil infusion was not discontinued during the laproscopic procedure. At week 12, this same patient developed worsening congestive heart failure requiring additional diuretics and the addition of an ACE inhibitor added to her medication regimen. Both SAEs were judged unlikely to be related to treprostinil.

Figure 8:
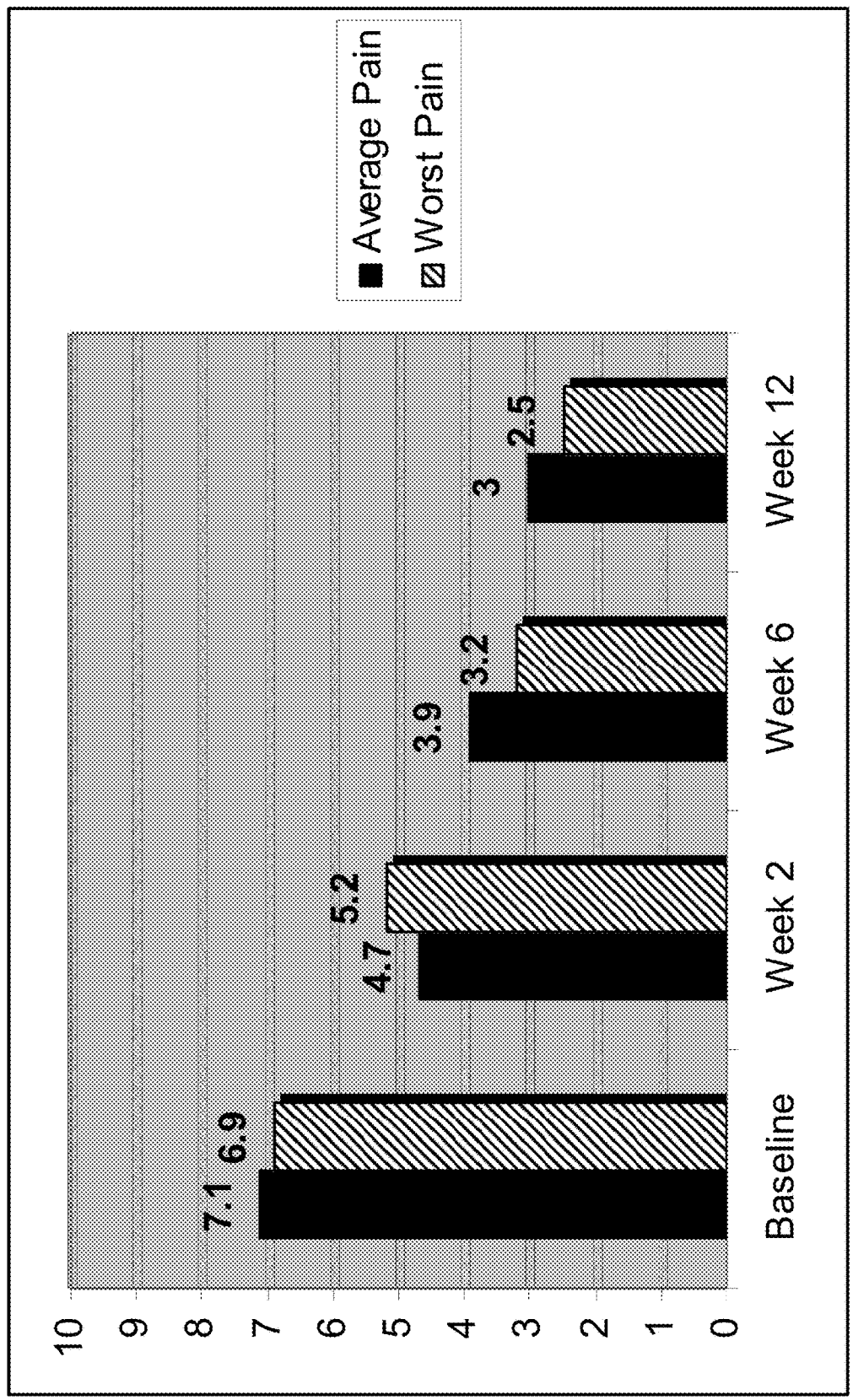
FIG. 8 shows patient assessed mean-average and worst rest pain rating.
Figure 9:
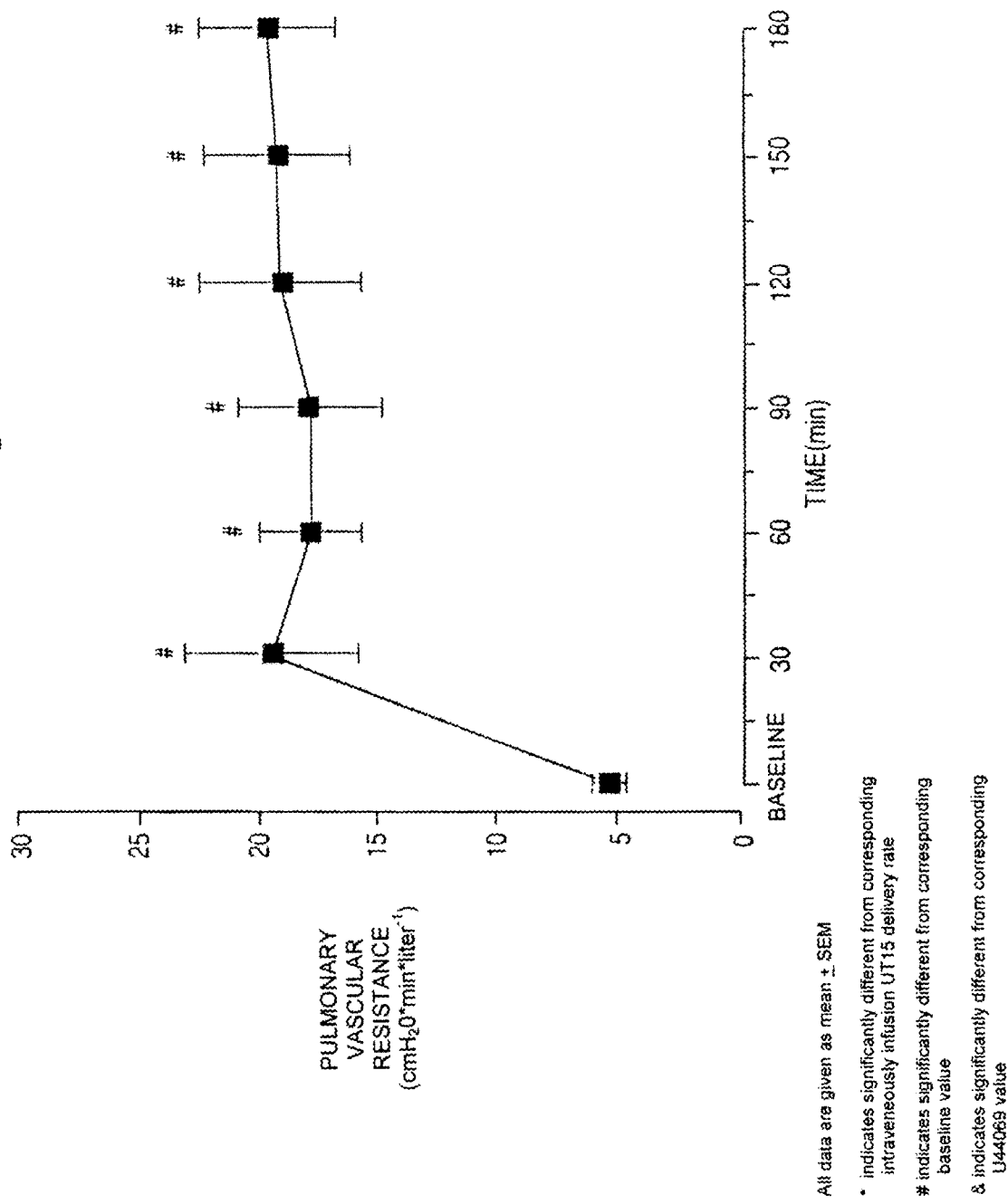
FIG. 9 is a graph of pulmonary vascular resistance ($cmH_2O$*min/liter) intravenously induced by U44069 over time (min).

Rest pain: There was a 64% reduction in the worst rest pain from baseline to week 12 (from mean of 8.4 to 2.5) and a 58% reduction in average rest pain from baseline to week 12 (from a mean of 7.1 to 2.4). FIG. 8 shows patient-assessed mean average and worst rest pain rating on the visual analog scales at scheduled study visits and the mean average rest pain over time during the study.

TABLE 3

Pain Medication Consumption

| Patient | Basline Pain Medication(s) | Week 2 | Week 6 | Week 12 |
|---|---|---|---|---|
| 1 | PERCOCET ® | No change | No change | No change |
| 2 | PERCOCET ® | Less | Less | No change |
| 3 | PERCOCET ® | No change | Less | No change |
| 4 | VICODIN ® | PERCOCET ® | Discontinued | |
| 5 | PERCOCET ® | No change | Less | Darvocet |
| 6 | VICODIN ® | Less | Less | PERCOCET ® |
| 7 | PERCOCET ® | Less | Less | None |
| 8 | PERCOCET ® | No change | Increased | No change |
| 9 | PERCOCET ® | No change | No change | |
| 10 | VICODIN ® | Less | None | None |

At baseline, all patients were on either oxycodone HCL/acetaminophen (PERCOCET® Endo Labs Inc) or hydrocodone bitartrate/acetaminophen (VICODIN®, Abbott Laboratories Inc.) to manage ischemic rest pain. At week 12, one patient had increased her consumption of pain medication, 4 patients medication usage was unchanged from baseline, three patients had reduced their pain medication consumption, one patient switched to a non-sedating, non-narcotic pain medication and two patients experienced complete pain relief and discontinued all pain medications. The patient who discontinued the study because of infusion site pain had experienced complete ischemic pain relief and had discontinued pain medication at week 6, but resumed pain medication one week after discontinuing treprostinil.

TABLE 4

Ischemic Wounds

| Patient | Reference Wound Location and description: Baseline | Wound Duration: | Wound Condition at 12 weeks |
|---|---|---|---|
| 1 | Right Lateral Ankle No gangrene Exposed Tendon 5 cm$^2$ | 9 months | Slightly larger |
| 2 | Left lateral Lower leg No gangrene 44 cm$^2$ | 4 months | Slightly larger |
| 3 | L Heel large amount of tissue loss with necrosis 63.7 cm$^2$ | 3 months | Slightly larger |
| 4 | L dorsum of foot No Gangrene 15 cm$^2$ | 9 months | Partially healed |
| 5 | L 5$^{th}$ Toe and documented osteomyelitis Able to probe to bone No gangrene 0.16 cm$^2$ | 2 months | Fully healed |
| 6 | Full thickness dry gangrene Left 3, 4, and 5$^{th}$ toes with large dorsal foot wound No measured | 3 months | No change |
| 7 | Ischemic breakdown R and L 3$^{rd}$ toe No gangrene <1.5 cm$^2$* | 1 month | Fully Healed |
| 8 | Gangrenous ulceration tip of L 2 toe 1.87 cm$^2$ | 3 months | No Change |
| 9 | L ulcer medial aspect lower leg with cellulites No gangrene 3.5 cm$^2$ | 2 months | Partially healed at six weeks‡ |
| 10 | Neuropathic ulceration R Great Toe No gangrene 1.96 cm$^2$ | 1 year | Fully healed at 12 weeks |

Wound healing: Wound tracings and investigator rating (worse, unchanged, improved, or completely healed) were used to evaluate ischemic wounds. However, the nature and location of most wounds prevented wound tracing. Wounds varied in location, extent of tissue loss and degree of gangrene or necrosis. The investigator evaluation of worse, unchanged, improved or completely healed was used in the final evaluation. All ten patients had at least on ischemic wound at baseline. Wound duration varied from four weeks to nine months. Wound size ranged from 0.16-63.7 cm$^2$. Three patients experienced complete healing of their wounds. Patient 5 demonstrated complete wound closure at week 6 and patient 7 and 10 demonstrated complete wound closure at week 12. No patient developed a new wound during the trial. Brief case reports for these patients are presented below. A fourth case report is presented which represents a unique use for prostacyclin. Treprostinil was used to delay amputation to allow the patient to complete rehabilitation for a fractured hip on the endangered limb.

Case 1

Patient 5 is an 88 year old female with peripheral vascular disease. An arteriogram shows a completely occluded left SFA with collaterals reconstituting the left popliteal artery. Her ABI at baseline was 0.30. She had a small ischemic ulcer on the left second toe for 2 months that measured 0.16 cm$^2$ and one could probe to the bone. An MRA noted osteomyelitis of the left second toe. She had complete wound closure at week 6. While her rest pain did not resolve completely, she changed from hydrocodone bitartrate/acetaminophen, to propoxyphene and acetaminophen. Her treprostinil dose was 15 ng/kg/min.

Case 2

Patient 7 is an 88 year old female who presented with non-healing ischemic wounds on the right and left third toe following toenail removal 4 weeks previously. She had bilateral renal angioplasty with stints in 2003. An arteriogram was deferred due to her renal status and creatinine of 2.7. The MRA showed diffuse infra-inguinal disease with two vessel run off to the foot. She was unable to walk any distance without leg pain and experienced severe ischemic rest pain. Her ABI at baseline were right 0.40 and left 0.36. At week 6 she had complete resolution of her rest pain, was able to walk without restrictions, and discontinued narcotic pain medication. At week 12 she had complete wound closure. Her treprostinil dose was 7.5 ng/kg/min.

Case 3

Patient 10 is a 65 year old male, insulin dependent diabetic, chronic renal insufficiency, and congestive heart failure with 13 year history of PAD. He had a right femoral popliteal by-pass in 1991 and documented occlusion 5 months later. He has had repeated neuropathic ulcerations of the right great toe that have never fully resolved since 2001 in the presence of PAD. He participated in previous trial of another prostanoid in late 2001 and demonstrated improvement in ulcer at the completion of the trial but it is unknown if he was on placebo or active drug. He began experiencing ischemic rest pain in his right leg in 2003. At baseline, he had a non-healing ulcer on his right great toe for 9 months measuring 1.96 cm². He completed 12 weeks of treprostinil and showed early wound healing with complete wound closure at week 12. He also experienced complete resolution of his ischemic rest pain at week 2 as well as severe claudication symptoms and discontinued his narcotic pain medications. His treprostinil dose was 15 ng/kg/min.

Case 4

Patient 3 is an 82 year old male with a history of oxygen dependent COPD, atrial fibrillation, hyperglycemia, anemia of unknown origin and multilevel vascular disease. His vascular disease history included transient ischemic attacks (TIA) requiring a carotid endarterectomy in 1995 and again in 2003, coronary artery disease requiring a coronary artery bypass in 1995, and documented peripheral artery disease since 2002. He broke his left hip in August 2003 and developed left heel and leg ischemic ulcers while in a rehabilitation facility. An ultrasound in November 2003 demonstrated distal right SFA stenosis, proximal left SFA mid SFA occlusion with large collaterals. Minimal flow was seen at the ankle level with toe pressure less than 40 mm/Hg. The right ABI was 0.58 and the left ABI was 0.25. The patient had two large ischemic wounds with extensive tissue loss located on the left heel (63.75 cm²) and left lateral leg (40.17 cm²). There was concern the patient would be unable to utilize a prosthetic limb following an amputation in the presence of the recent hip fracture and incomplete healing of the prosthetic hip. He was enrolled in the study to stabilize the wounds, provided rest pain relief, delay amputation and continue the rehabilitation of the left hip. His wounds remained stable during the twelve weeks of drug treatment with no significant improvement, however, no worsening. Average rest pain scores were 7 at baseline and reduced to 4. Worst rest pain scores reduced from 8 to 4. He reduced his pain medication consumption from hydrocodone bitartrate/acetaminophen, and oxycontin to oxycodone HCL/acetaminophen alone. He was able to complete rehabilitation of his left hip and it is anticipated he will be able to utilize a prosthetic limb following a BKA as a result of this extra time for rehabilitation therapy.

Conclusions:

This open-label study supports the safety of treprostinil infusion. The patients enrolled in this study reflected the demographics seen with this end stage presentation of PAD. This is a heterogeneous population with significant co-morbid disorders contributing to the overall disease process. These patients are the worst of the worst with impending amputations.

Ischemic pain and wounds are the primary management problem in patients with CLI. Treprostinil provided pain relief in all patients as well as wound healing in three patients. The patients who failed to demonstrate healing had large wounds with necrosis and/or gangrene. While the three patients who demonstrated complete healing had less tissue loss, one would anticipate they would have deteriorated given their extensive vascular disease and lack of surgical revascularization options.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

I claim:

1. A method of treating a human patient suffering from pulmonary hypertension, comprising:
   providing an infusion solution comprising 0.1 to 5% w/v of treprostinil or a pharmaceutically acceptable salt or ester thereof, and
   intravenously administering the infusion solution to the human patient at a rate of from 0.625 to 50 ng/kg/min, wherein the infusion solution is sterile and isotonic with blood.

2. The method of claim 1, wherein the infusion solution is administered at a rate of 0.1 ml/min/kg.

3. The method of claim 1, wherein the rate of administration is from 10 to 15 ng/kg/min.

* * * * *